United States Patent
Ohkubo

(10) Patent No.: US 12,281,292 B2
(45) Date of Patent: Apr. 22, 2025

(54) CELL CULTURE DEVICE AND CELL CULTURE METHOD

(71) Applicant: SHIMADZU CORPORATION, Kyoto (JP)

(72) Inventor: Tomoki Ohkubo, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 1014 days.

(21) Appl. No.: 17/050,913

(22) PCT Filed: May 29, 2019

(86) PCT No.: PCT/JP2019/021389
§ 371 (c)(1),
(2) Date: Oct. 27, 2020

(87) PCT Pub. No.: WO2019/235336
PCT Pub. Date: Dec. 12, 2019

(65) Prior Publication Data
US 2021/0230529 A1    Jul. 29, 2021

(30) Foreign Application Priority Data
Jun. 8, 2018 (JP) .................. 2018-110359

(51) Int. Cl.
C12M 1/00 (2006.01)
C12M 1/26 (2006.01)
C12M 3/00 (2006.01)

(52) U.S. Cl.
CPC ............ *C12M 23/26* (2013.01); *C12M 23/48* (2013.01); *C12M 33/00* (2013.01)

(58) Field of Classification Search
CPC ................... C12M 25/04; C12M 23/12; B01L 2300/0812; B01L 2300/0829
See application file for complete search history.

(56) References Cited

U.S. PATENT DOCUMENTS

| | | | |
|---|---|---|---|
| 3,102,082 | A | 8/1963 | Brewer |
| 3,853,712 | A | 12/1974 | House et al. |
| 3,948,732 | A | 4/1976 | Haddad et al. |
| 5,786,215 | A | 7/1998 | Brown et al. |

FOREIGN PATENT DOCUMENTS

CN    106497786 A    3/2017
JP    2014224679 A * 12/2014    ........ B01L 3/502707

OTHER PUBLICATIONS

International Search Report for PCT/JP2019/021389 dated Aug. 13, 2019 [PCT/ISA/210].

(Continued)

*Primary Examiner* — Jonathan M Hurst
(74) *Attorney, Agent, or Firm* — Suchrue Mion, PLLC

(57) ABSTRACT

A cell culture device (100) includes a band-shaped flexible member (10), the band-shaped member being configured to be circumferentially windable. The band-shaped member (10) has an inner circumferential surface (1a) and an outer circumferential surface (1b), at least one of which is provided with a plurality of wells (2) each having a concave shape, and at least some (2) of the plurality of wells (2) are connected to each other by a culture solution conduit (3).

15 Claims, 14 Drawing Sheets

(56) References Cited

OTHER PUBLICATIONS

Written Opinion for PCT/JP2019/021389 dated Aug. 13, 2019 [PCT/ISA/237].
Communication dated Dec. 1, 2023, issued by the Chinese Patent Office in Chinese Application No. 201980030950.X.
Yaxiong Liu, et al., "The fabrication and cell culture of three-dimensional rolled scaffolds with complex micro-architectures", Biofabrication, Jan. 18, 2012, pp. 1-14 (16 pages total).
Office Action issued Jun. 1, 2024 in Chinese Application No. 201980030950.X.

\* cited by examiner

FIRST EMBODIMENT

SECOND EMBODIMENT

SECOND EMBODIMENT

THIRD EMBODIMENT

THIRD EMBODIMENT

THIRD EMBODIMENT

THIRD EMBODIMENT

MODIFIED EXAMPLE OF SECOND EMBODIMENT

FIG.21
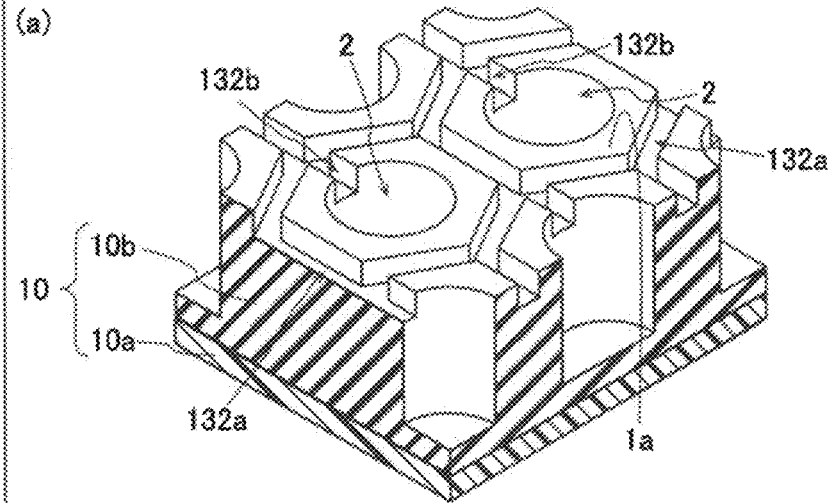
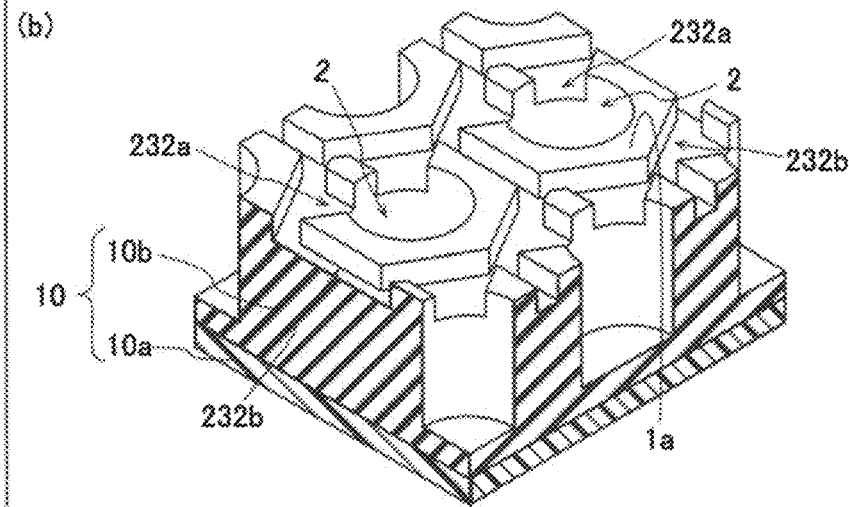
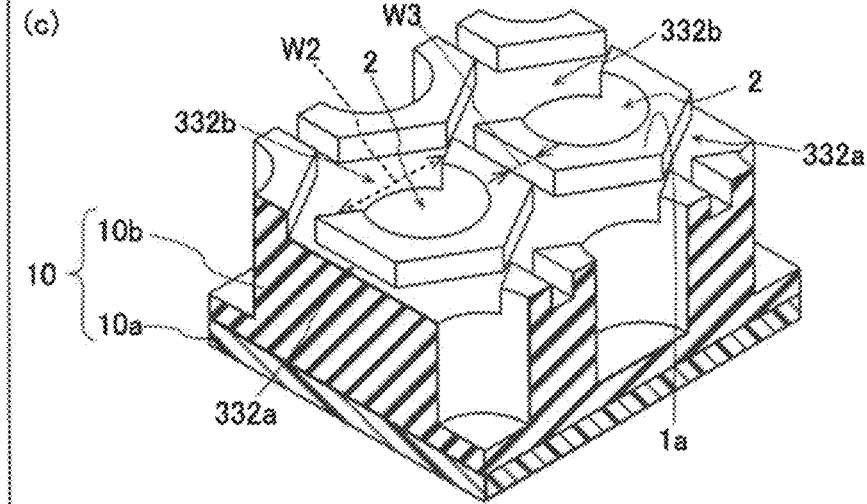

MODIFIED EXAMPLE OF FIRST TO THIRD EMBODIMENTS

MODIFIED EXAMPLE OF THIRD EMBODIMENT

CELL CULTURE DEVICE AND CELL CULTURE METHOD

TECHNICAL FIELD

The present invention relates to a cell culture device and a cell culture method, and more particularly, it relates to a cell culture device that cultures cells on the circumferential surface of a band-shaped member configured to be circumferentially windable and a cell culture method.

BACKGROUND ART

Conventionally, a cell culture device configured to culture cells on the circumferential surface of a circumferentially windable band-shaped member and a cell culture method for culturing the cells on the circumferential surface of the circumferentially windable band-shaped member are known. Such a cell culture device and a cell culture method are disclosed in U.S. Pat. Nos. 3,102,082, 3,853,712, 3,948,732, and 5,786,215, for example.

In the cell culture device disclosed in each of U.S. Pat. Nos. 3,102,082, 3,853,712, 3,948,732, and 5,786,215, cells are seeded on the circumferential surface of the band-shaped member configured to be circumferentially windable. The cells are seeded on the circumferential surface of the band-shaped member such that it is easy to increase an area over which the cells are seeded, and thus a large number of cells can be seeded (cultured).

The cells adhere to the circumferential surface of the band-shaped member, which is adhesive to cells to be seeded. Furthermore, the circumferential surface of the band-shaped member on which the cells are seeded is flat, and the cells can adhere to arbitrary locations on the circumferential surface. In a state in which the cells are seeded on the circumferential surface of the band-shaped member, a culture solution is introduced into the band-shaped member circumferential wound such that the cells are cultured.

PRIOR ART

Patent Document

Patent Document 1: U.S. Pat. No. 3,102,082
Patent Document 2: U.S. Pat. No. 3,853,712
Patent Document 3: U.S. Pat. No. 3,948,732
Patent Document 4: U.S. Pat. No. 5,786,215

SUMMARY OF THE INVENTION

Problem to be Solved by the Invention

However, in the cell culture device disclosed in each of U.S. Pat. Nos. 3,102,082, 3,853,712, 3,948,732, and 5,786,215, the circumferential surface (inner circumferential surface and outer circumferential surface) of the band-shaped member on which the cells are seeded is flat, and the cells adhere to arbitrary locations on the circumferential surface such that it is difficult to control where the cells are seeded (adhere). Consequently, depending on locations on the circumferential surface, the density (or sparseness) of the seeded and cultured cells may vary. In this case, the cells are seeded on the band-shaped member such that a large number of cells can be seeded (cultured), but it is difficult to achieve a uniform density of the seeded (cultured) cells.

The present invention is intended to solve the above problem. The present invention aims to provide a cell culture device and a cell culture method capable of achieving a uniform density of seeded (cultured) cells while a large number of cells are seeded (cultured).

Means for Solving the Problems

In order to attain the aforementioned object, a cell culture device according to a first aspect of the present invention includes a band-shaped flexible member, the band-shaped member being configured to be circumferentially windable, in a state in which the band-shaped member is circumferentially wound, the band-shaped member has an inner circumferential surface and an outer circumferential surface, at least one of which is provided with a plurality of wells each having a concave shape, the plurality of wells adjusted for cells to be cultured therein, and at least some of the plurality of wells are connected to each other by a culture solution conduit adjusted for a culture solution to flow therethrough.

In the cell culture device according to the first aspect of the present invention, as described above, the plurality of concave wells adjusted for the cells to be cultured therein are provided on the circumferential surface of the band-shaped member, and the plurality of wells are connected to each other by the culture solution conduit such that the cells can be seeded in each of the plurality of concave wells, and the cells seeded in each of the plurality of wells can be cultured with the culture solution that flows through the culture solution conduit. The number (or amount) of cells to be cultured is determined according to the sizes of the wells, and thus the number of cells to be cultured in each of the plurality of wells can be uniform when the size of each of the plurality of wells is uniform. Consequently, a variation in the density of the cells seeded and cultured on the circumferential surface can be significantly reduced or prevented. Thus, a uniform density of the seeded (cultured) cells can be achieved while a large number of cells are seeded (cultured) on the circumferential surface of the band-shaped member.

In the aforementioned cell culture device according to the first aspect, in the state in which the band-shaped member is circumferentially wound, the plurality of wells and the culture solution conduit are preferably provided on the inner circumferential surface of the band-shaped member, and are preferably covered by the outer circumferential surface of the band-shaped member wound on an inner circumferential side of the plurality of wells and the culture solution conduit. Accordingly, the outer circumferential surface of the band-shaped member wound on the inner circumferential side can cover (seal) the plurality of wells and the culture solution conduit, and thus leakage of the culture solution from the wells and the culture solution conduit can be significantly reduced or prevented. Furthermore, an increase in the number of components can be significantly reduced or prevented as compared with a case in which a member separate from the band-shaped member is used to cover the plurality of wells and the culture solution conduit.

In this case, neither the plurality of wells nor the culture solution conduit is preferably provided on the inner circumferential surface of the band-shaped member wound on an innermost circumference of the band-shaped member circumferentially wound, and the plurality of wells and the culture solution conduit are preferably provided on the inner circumferential surface of the band-shaped member wound on an outer circumferential side of the band-shaped member wound on the innermost circumference. Accordingly, the plurality of wells and the culture solution conduit are not provided on the circumferential surface of the band-shaped member wound on the innermost circumference, and thus the culture solution does not flow on the circumferential surface of the band-shaped member wound on the innermost circumference. The band-shaped member is not provided on the inner circumferential side of the band-shaped member wound on the innermost circumference, and thus when the plurality of wells and the culture solution conduit are provided on the circumferential surface of the band-shaped member on the innermost circumference, the wells and the culture solution conduit on the circumferential surface of the band-shaped member on the innermost circumference are not covered by the band-shaped member from the inner circumferential side. In this case, the culture solution may leak from the circumferential surface of the band-shaped member on the innermost circumference. Therefore, the plurality of wells and the culture solution conduit are not provided on the circumferential surface of the band-shaped member on the innermost circumference, and thus the culture solution can be prevented from leaking from the circumferential surface of the band-shaped member on the innermost circumference.

The aforementioned cell culture device including the plurality of wells and the culture solution conduit provided on the inner circumferential surface of the band-shaped member preferably further includes a first core configured to extend along a central axis of a winding of the band-shaped member, and the plurality of wells and the culture solution conduit provided on the inner circumferential surface of the band-shaped member wound on an innermost circumference of the band-shaped member circumferentially wound are preferably covered by a circumferential surface of the core. Accordingly, the core can significantly reduce or prevent leakage of the culture solution from the plurality of wells and the culture solution conduit provided on the inner circumferential surface of the band-shaped member wound on the innermost circumference.

In the aforementioned cell culture device according to the first aspect, in a state in which the band-shaped member circumferentially wound is arranged such that a central axis of a winding is along a vertical direction, the culture solution conduit preferably includes an introduction conduit configured to connect the plurality of wells arranged at an upper end of the band-shaped member and in a vicinity of the upper end, the introduction conduit being adjusted for the culture solution to be introduced thereinto, a discharge conduit configured to connect the plurality of wells arranged at a lower end of the band-shaped member and in a vicinity of the lower end, the discharge conduit being adjusted for the culture solution to be discharged therethrough, and a connection conduit configured to connect at least some of the plurality of wells to each other. Accordingly, the culture solution can be easily introduced into the wells arranged in the vicinity of the upper end of the band-shaped member through the introduction conduit, and the culture solution can be easily discharged from the wells arranged in the vicinity of the lower end of the band-shaped member through the discharge conduit. Furthermore, the introduced culture solution can easily flow into each of the plurality of wells through the connection conduit. Note that the vicinity of the end refers to the vicinity of the position of the end.

In this case, the connection conduit is preferably configured to connect upper portions of the plurality of wells to each other in the state in which the band-shaped member circumferentially wound is arranged such that the central axis of the winding is along the vertical direction. Accordingly, the culture solution flows downward from above during culturing of the cells, and thus unlike a case in which the connection conduit connects lower portions of the plurality of wells to each other, discharge of the cells contained in the wells from the wells via the connection conduit due to the downward flow of the culture solution can be significantly reduced or prevented.

In the aforementioned cell culture device including the culture solution conduit including the introduction conduit, the discharge conduit, and the connection conduit, in the state in which the band-shaped member circumferentially wound is arranged such that the central axis of the winding is along the vertical direction, the introduction conduit is preferably connected to an upper portion of each of the plurality of wells arranged in the vicinity of the upper end, and the discharge conduit is preferably connected to an upper portion of each of the plurality of wells arranged in the vicinity of the lower end via the connection conduit. Accordingly, both the introduction conduit and the discharge conduit are connected to the upper portions of the wells, and thus discharge of the cells contained in the plurality of wells arranged in the vicinity of the upper end of the band-shaped member and the plurality of wells arranged in the vicinity of the lower end of the band-shaped member from the wells due to the flow of the culture solution can be significantly reduced or prevented.

In the aforementioned cell culture device including the culture solution conduit including the introduction conduit, the discharge conduit, and the connection conduit, in the state in which the band-shaped member circumferentially wound is arranged such that the central axis of the winding is along the vertical direction, the connection conduit is preferably inclined upward from an upper portion of each of the plurality of wells toward an adjacent well. Accordingly, a force acts downward on the cells due to their own weights, and thus as compared with a case in which the connection conduit is inclined downward from the wells, discharge of the cells contained in the wells from the wells via the connection conduit can be effectively significantly reduced or prevented.

In the aforementioned cell culture device according to the first aspect, the plurality of wells are preferably provided in a staggered manner on a circumferential surface of the band-shaped member. Accordingly, as compared with a case in which the plurality of wells are provided in a matrix, the plurality of wells can be densely arranged on the circumferential surface of the band-shaped member. Consequently, the sizes of the wells can be easily increased. Moreover, the number of wells can be easily increased. Note that the staggered manner refers to an arrangement in which wells in adjacent rows are misaligned in a predetermined direction when a plurality of rows of wells arranged along the predetermined direction are arranged side by side so as to be adjacent to each other along a direction orthogonal to the predetermined direction.

In the aforementioned cell culture device according to the first aspect, a circumferential surface of the band-shaped member provided with the plurality of wells is preferably non-adhesive to the cells. Accordingly, it becomes difficult for the cells to adhere to the wells, and thus the cells can easily adhere (or adsorb) to each other in the wells. Consequently, a mass of the cells can be easily formed.

The aforementioned cell culture device according to the first aspect preferably further includes a collection container configured to store a solution through which the band-shaped member unwound from a circumferentially wound state passes, the collection container being configured to collect the cells contained in the wells of the band-shaped member that passes through the solution. Accordingly, the cells can be collected while exposure of the cultured cells to the air is significantly reduced or prevented.

In this case, the collection container is preferably configured to collect, from the plurality of wells of the band-shaped member that passes through the solution while openings of the plurality of wells face downward, the cells that settle in the solution due to their own weights. Accordingly, the cells can be collected by settling due to their own weights, and thus it is not necessary to use a dedicated member for carrying the cells to the collection container. Consequently, an increase in the number of components can be significantly reduced or prevented in collecting the cells.

The aforementioned cell culture device including the collection container preferably further includes a first cell picking unit configured to pick the cells from the plurality of wells of the band-shaped member that passes through the solution while openings of the plurality of wells face upward. Accordingly, the cells can be collected more reliably by the first cell picking unit as compared with a case in which the cells settle downward due to their own weights and are collected.

In this case, the first cell picking unit preferably includes a cell suction unit configured to suction the cells from the plurality of wells of the band-shaped member that passes through the solution. Accordingly, damage and deterioration of the cells can be significantly reduced or prevented as compared with a case in which the cells are directly picked by an instrument.

The aforementioned cell culture device according to the first aspect preferably further includes a second core configured to extend along a central axis of a winding of the band-shaped member, a third core provided separately from the second core, the third core being configured to extend along the central axis of the winding of the band-shaped member, the third core being adjusted for the band-shaped member unwound from the second core to be wound therearound, and a housing configured to house the band-shaped member, at least a portion of the second core, and at least a portion of the third core, the second core is preferably adjusted for the band-shaped member unwound from the third core to be wound therearound, and the housing preferably includes an opening adjusted for the cells to be introduced into the band-shaped member being wound around the third core from the second core inside the housing, the opening being adjusted for the cells to be picked from the band-shaped member being wound around the second core from the third core inside the housing. Accordingly, the second core and the third core are used such that both the introduction of the cells and the picking of the cells can be performed. Consequently, the configuration of the cell culture device can be simplified as compared with a case in which one of the introduction of the cells and the picking of the cells is performed using a member other than the second core and the third core.

Furthermore, the introduction of the cells and the picking of the cells are performed via the opening of the housing such that both the introduction of the cells and the picking of the cells can be performed while the band-shaped member is placed inside the housing. Consequently, as compared with a case in which the band-shaped member is moved to the outside of the housing and one of the introduction of the cells and the picking of the cells is performed, a device space can be saved while the configuration of the cell culture device can be further simplified.

In this case, the housing preferably includes a guide configured to guide the band-shaped member being wound around the second core and the third core such that the band-shaped member is exposed via the opening inside the housing. Accordingly, the band-shaped member being wound around the second core and the third core is exposed via the opening by the guide, and thus the introduction of the cells and the picking of the cells performed on the band-shaped member via the opening can be facilitated.

The aforementioned cell culture device including the housing including the guide preferably further includes a cell introduction unit configured to introduce the cells via the opening into each of the plurality of wells of the band-shaped member being wound around the third core from the second core while being guided by the guide, and a second cell picking unit configured to pick the cells via the opening from the plurality of wells of the band-shaped member being wound around the second core from the third core while being guided by the guide. Accordingly, the cell introduction unit is used such that the cells can be easily introduced into the wells of the band-shaped member as compared with a case in which the cells are introduced into the wells by manually dropping a cell suspension. Furthermore, the second cell picking unit is used such that the cells can be easily picked from the wells as compared with a case in which the cells settle downward in the housing due to their own weights and are collected from the housing.

In the aforementioned cell culture device including the housing including the guide, the opening is preferably configured to be openable and closable. Accordingly, the housing can be easily switched between a closed state and an open state.

A cell culture method according to a second aspect of the present invention includes seeding cells in each of a plurality of wells each having a concave shape of a band-shaped flexible member, the band-shaped member being configured to be circumferentially windable, circumferentially winding the band-shaped member after the seeding the cells, and flowing a culture solution into each of the plurality of wells via a culture solution conduit from an upper side of the band-shaped member circumferentially wound in a state in which the band-shaped member circumferentially wound is arranged such that a central axis of a winding is along a vertical direction after the circumferentially winding the band-shaped member, the band-shaped member has an inner circumferential surface and an outer circumferential surface, at least one of which is provided with the plurality of wells adjusted for the cells to be cultured therein, and at least some of the plurality of wells are connected to each other by the culture solution conduit adjusted for the culture solution to flow therethrough.

In the cell culture method according to the second aspect of the present invention, as described above, the cells are seeded and cultured using the band-shaped member having the circumferential surface provided with the plurality of wells adjusted for the cells to be cultured therein and the culture solution conduit configured to connect the plurality of wells to each other. Thus, a uniform density of the seeded (cultured) cells can be achieved while a large number of cells are seeded (cultured) on the circumferential surface of the band-shaped member.

The aforementioned cell culture method according to the second aspect preferably further includes unwinding the band-shaped member circumferentially wound after culturing the cells and collecting the cells contained in the wells while passing the band-shaped member that has been unwound through a solution stored in a collection container. Accordingly, exposure of the cells to the air during collection of the cultured cells can be significantly reduced or prevented. Consequently, deterioration of the cells during collection of the cells can be significantly reduced or prevented.

The aforementioned cell culture method according to the second aspect preferably further includes winding the band-shaped member around a first side core including at least a portion housed in a housing, the first side core being configured to extend along the central axis of the winding of the band-shaped member, the seeding the cells preferably includes introducing the cells via an opening provided on the housing into the band-shaped member being wound, inside the housing, around a second side core provided separately from the first side core, the second side core including at least a portion housed in the housing, the second side core being configured to extend along the central axis of the winding of the band-shaped member, while winding, around the second side core, the band-shaped member wound around the first side core, the winding the band-shaped member after the seeding the cells preferably includes winding the band-shaped member around the second side core inside the housing after the introducing the cells into the band-shaped member, and the flowing the culture solution into each of the plurality of wells preferably includes flowing the culture solution into each of the plurality of wells by introducing the culture solution into the band-shaped member wound around the second side core inside the housing after the introducing the cells. Accordingly, each of the introducing the cells and the flowing the culture solution can be performed while the band-shaped member is placed inside the housing. Consequently, as compared with a case in which the band-shaped member is moved to the outside of the housing and one of the introducing the cells and the flowing the culture solution is performed, the working time required to perform cell culture can be shortened by the time required to move the band-shaped member.

In this case, the cell culture method preferably further includes picking the cells via the opening from the band-shaped member being wound around the first side core inside the housing while winding, around the first side core, the band-shaped member wound around the second side core after the culture solution flows through the band-shaped member. Accordingly, the first side core and the second side core are used such that both the introduction of the cells and the picking of the cells can be performed. Consequently, it is possible to provide the cell culture method that enables simplification of the configuration of the cell culture device as compared with a case in which one of the introduction of the cells and the picking of the cells is performed using a member other than the first side core and the second side core.

In the aforementioned cell culture method including the picking the cells from the band-shaped member being wound around the first side core, the introducing the cells preferably includes introducing the cells into the band-shaped member being wound around the second side core inside the housing in a state in which the housing is filled with a solution, the flowing the culture solution into each of the plurality of wells preferably includes flowing the culture solution into each of the plurality of wells of the band-shaped member wound around the second side core inside the housing in a state in which the solution has been discharged from the housing after the introducing the cells into the band-shaped member, and the picking the cells preferably includes picking the cells from the band-shaped member being wound around the first side core inside the housing in the state in which the housing is filled with the solution after the flowing the culture solution into each of the plurality of wells. Accordingly, the cells are introduced into the band-shaped member in a state in which the housing is filled with the solution such that the cells can be introduced (seeded) into the wells while inclusion of air bubbles in the wells of the band-shaped member is significantly reduced or prevented. Thus, seeding of the cells in the wells can be more reliably performed. Furthermore, the culture solution flows through the wells in a state in which the solution inside the housing has been discharged such that as compared with a case in which the housing is filled with the solution such that the band-shaped member is immersed in the solution, the culture solution in the wells can be more efficiently circulated. In addition, the cells are picked from the band-shaped member in a state in which the housing is filled with the solution such that the cells can be picked from the housing while exposure of the cultured cells to the air is significantly reduced or prevented.

Effect of the Invention

According to the present invention, as described above, it is possible to achieve a uniform density of the seeded (cultured) cells while a large number of cells are seeded (cultured).

BRIEF DESCRIPTION OF THE DRAWINGS

FIG. 21 is sectional perspective views showing the configuration of wells and culture solution conduits of a cell culture device according to modified examples of the first to third embodiments.

MODES FOR CARRYING OUT THE INVENTION

Embodiments embodying the present invention are hereinafter described on the basis of the drawings.

First Embodiment

The configuration of a cell culture device 100 according to a first embodiment is described with reference to FIGS. 1 to 10.

The cell culture device 100 is used in the field of drug discovery and basic research in biology, for example, and is expected to be applied to the field of regenerative medicine, for example. Specifically, it is applicable to induction of differentiation of pluripotent stem cell-derived tissues for transplantation therapy, expansion of pluripotent stem cells for transplantation therapy, and induction of differentiation of pluripotent stem cell-derived tissues for drug screening, for example.

Configuration of Cell Culture Device

Figure 1:
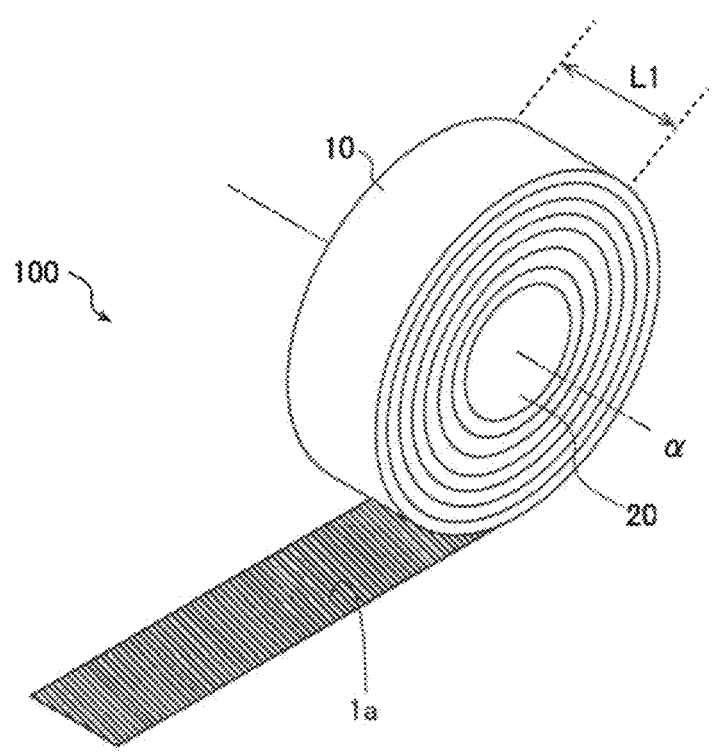
FIG. 1 is a perspective view showing the configuration of a tape of a cell culture device according to a first embodiment.

As shown in FIG. 1, the cell culture device 100 includes a flexible microarray tape (hereinafter simply referred to as a tape 10) that is circumferentially windable. The tape 10 has a band shape, and is circumferentially wound around a core 20 having a cylindrical shape a plurality of times. The tape 10 and the core 20 have substantially the same length L1 in a direction along the central axis α of a winding described below. The tape 10 is configured such that a tape body 10b (see FIG. 3) made of silicone rubber is stacked on a film 10a (see FIG. 3) made of plastic. The tape 10 is an example of a "band-shaped member" in the claims. The core 20 is an example of a "first core" in the claims.

Figure 11:
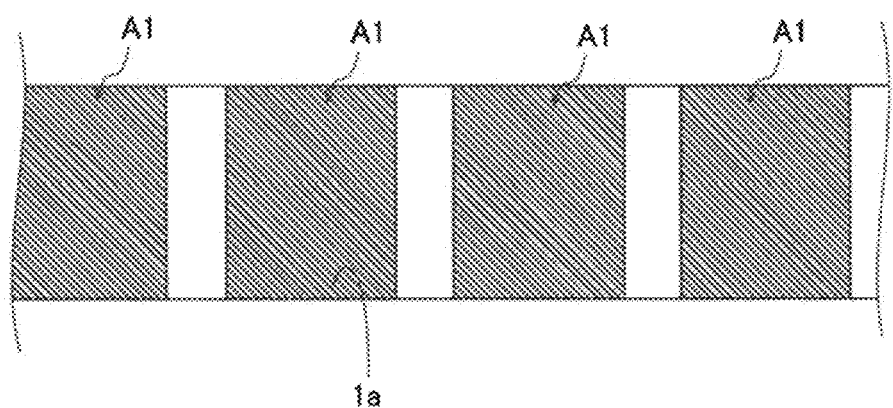
FIG. 11 is a diagram showing a well group provided on the inner circumferential surface of the tape in the cell culture device according to the first to third embodiments.

In the first embodiment, a plurality of wells 2 (see FIGS. 2 and 3) in which cells 101 are cultured are provided on the inner circumferential surface 1a of the tape 10 in a state in which the tape 10 is circumferentially wound. The wells 2 each have a concave shape such that the cells 101 are contained (seeded) therein. Furthermore, at least some of the plurality of wells 2 are connected to each other by culture solution conduits 3 (see FIG. 3) through which a culture solution flows. Specifically, the inner circumferential surface 1a of the tape 10 is provided with a plurality of well groups A1 (see hatched portions in FIG. 11) each including a plurality of wells 2 connected to each other by the culture solution conduits 3. The plurality of wells 2 have the same configuration (size) as each other. The cells 101 are induced pluripotent stem (IPS) cells or embryonic stem (ES) cells, for example. The inner circumferential surface 1a is an example of a "circumferential surface" in the claims.

Figure 2:
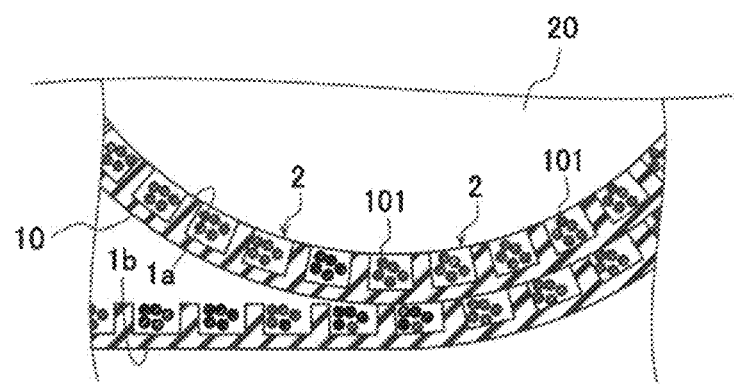
FIG. 2 is an enlarged sectional view showing the configuration of a tape of a cell culture device according to first and second embodiments.
Figure 3:
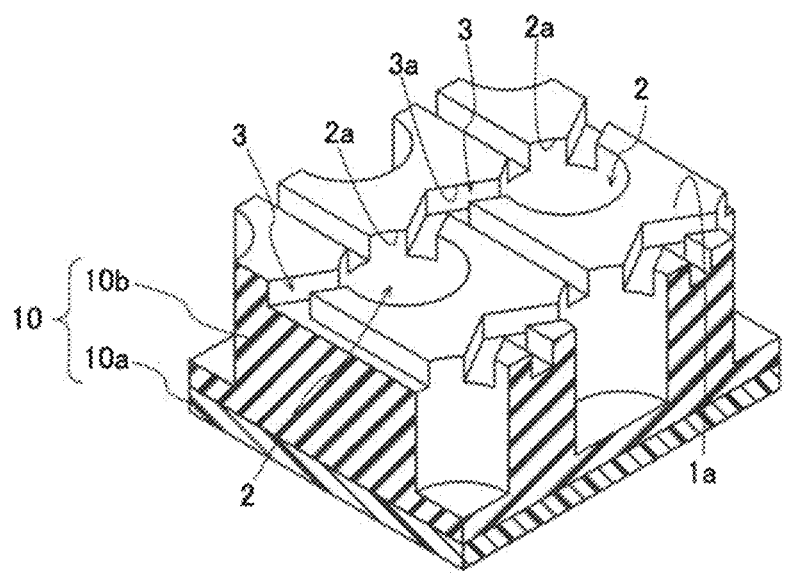
FIG. 3 is a sectional perspective view showing the configuration of wells and culture solution conduits of a cell culture device according to first to third embodiments.

As shown in FIG. 2, in a state in which the tape 10 is circumferentially wound, the plurality of wells 2 and the culture solution conduits 3 (see FIG. 3) are disposed on the inner circumferential side (core 20 side) of the tape 10. The plurality of wells 2 and the culture solution conduits 3 are covered by the outer circumferential surface 1b of the tape 10 wound on the inner circumferential side of the plurality of wells 2 and the culture solution conduits 3. Each of the plurality of wells 2 is provided such that openings 2a (see FIG. 3) are exposed on the inner circumferential surface 1a.

Furthermore, in the culture solution conduits 3, open ends 3a (see FIG. 3) are exposed on the inner circumferential surface 1a. That is, the outer circumferential surface 1b of the tape 10 wound on the inner circumferential side closes the openings 2a of the plurality of wells 2 and the open ends 3a of the culture solution conduits 3 from the inner circumferential side.

The inner circumferential surface 1a of the tape 10 provided with the plurality of wells 2 is non-adhesive to the cells 101. Specifically, the inner circumferential surface 1a of the tape 10 is coated with a polymer that is non-adhesive to cells.

Figure 4:
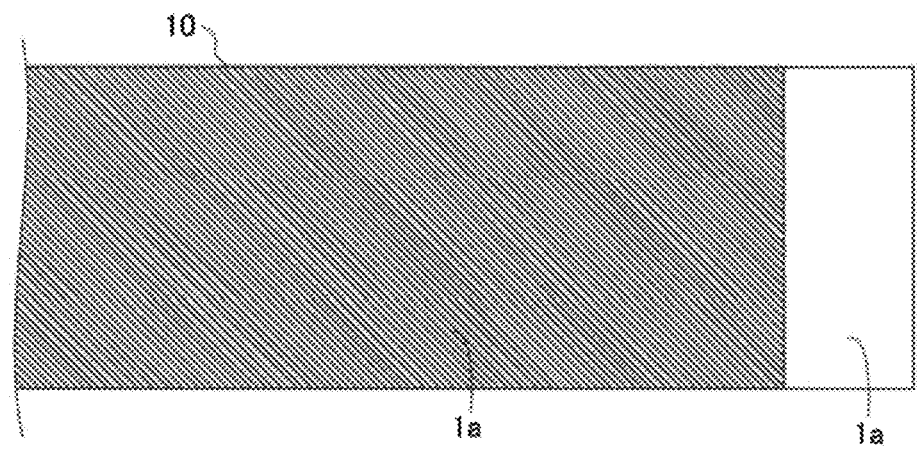
FIG. 4 is a diagram of an unwound band-shaped tape as viewed from the front side in the cell culture device according to the first to third embodiments.

As shown in FIG. 4, the plurality of wells 2 and the culture solution conduits 3 are not provided on the inner circumferential surface 1a (a non-hatched portion in FIG. 4) of a tape 10 wound on the innermost circumference of the tape 10 circumferentially wound. The plurality of wells 2 and the culture solution conduits 3 are provided on the inner circumferential surface 1a (a hatched portion in FIG. 4) of a tape 10 wound on the outer circumferential side of the tape 10 wound on the innermost circumference. That is, the inner circumferential surface 1a of the tape 10 wound on the innermost circumference is covered by the outer circumferential surface of the core 20 (see FIG. 2) from the inner circumferential side. All the wells 2 and the culture solution conduits 3 provided on the tape 10 are covered by the outer circumferential surface 1b (see FIG. 2) of the tape 10 from the inner circumferential side. The tape 10 having an inner circumferential surface 1a not provided with the plurality of wells 2 and the culture solution conduits 3 may be wound on the second circumference from the innermost circumference in addition to the innermost circumference, for example.

Figure 5:
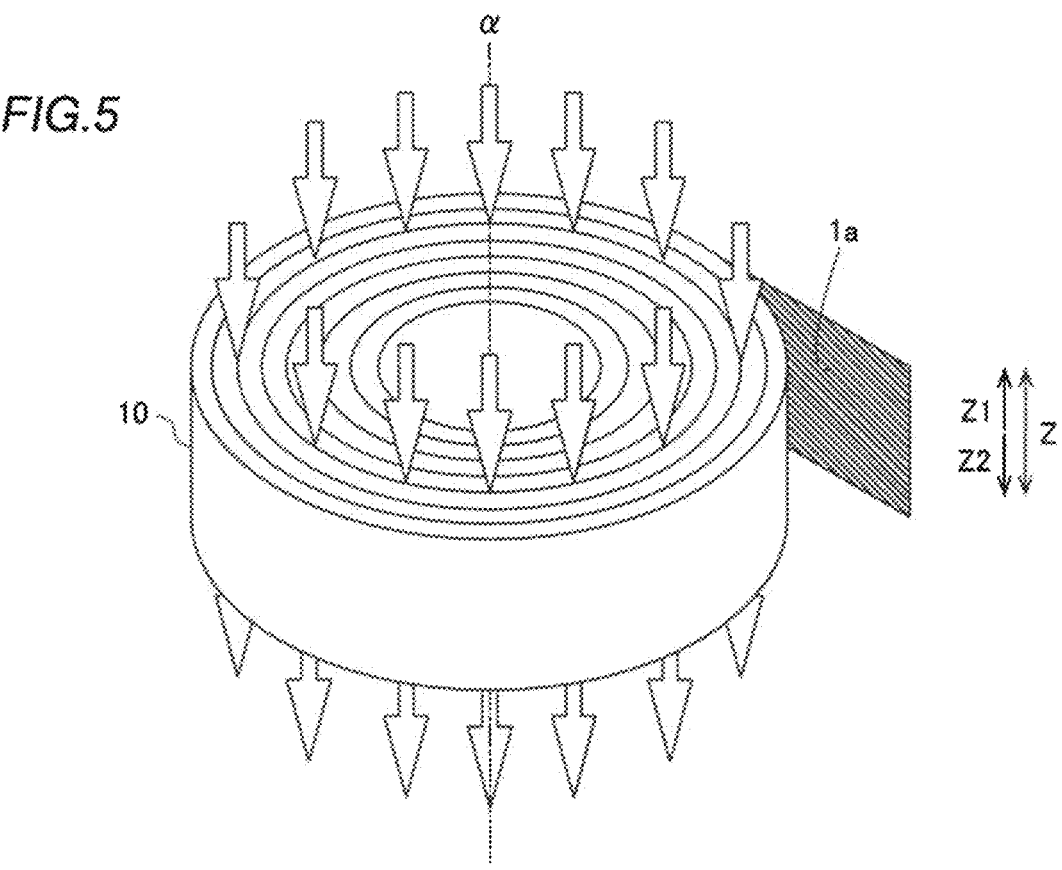
FIG. 5 is a diagram for illustrating a method for introducing a culture solution in the cell culture device according to the first and second embodiments.

As shown in FIG. 5, at the time of culturing the cells 101, the tape 10 circumferentially wound is arranged such that the central axis x of the winding is along a vertical direction (Z direction). The culture solution is introduced from the upper side (Z1 direction side) of the tape 10 circumferentially wound, and is discharged from the lower side (Z2 direction side). The Z direction is an example of a "vertical direction" in the claims.

Figure 6:
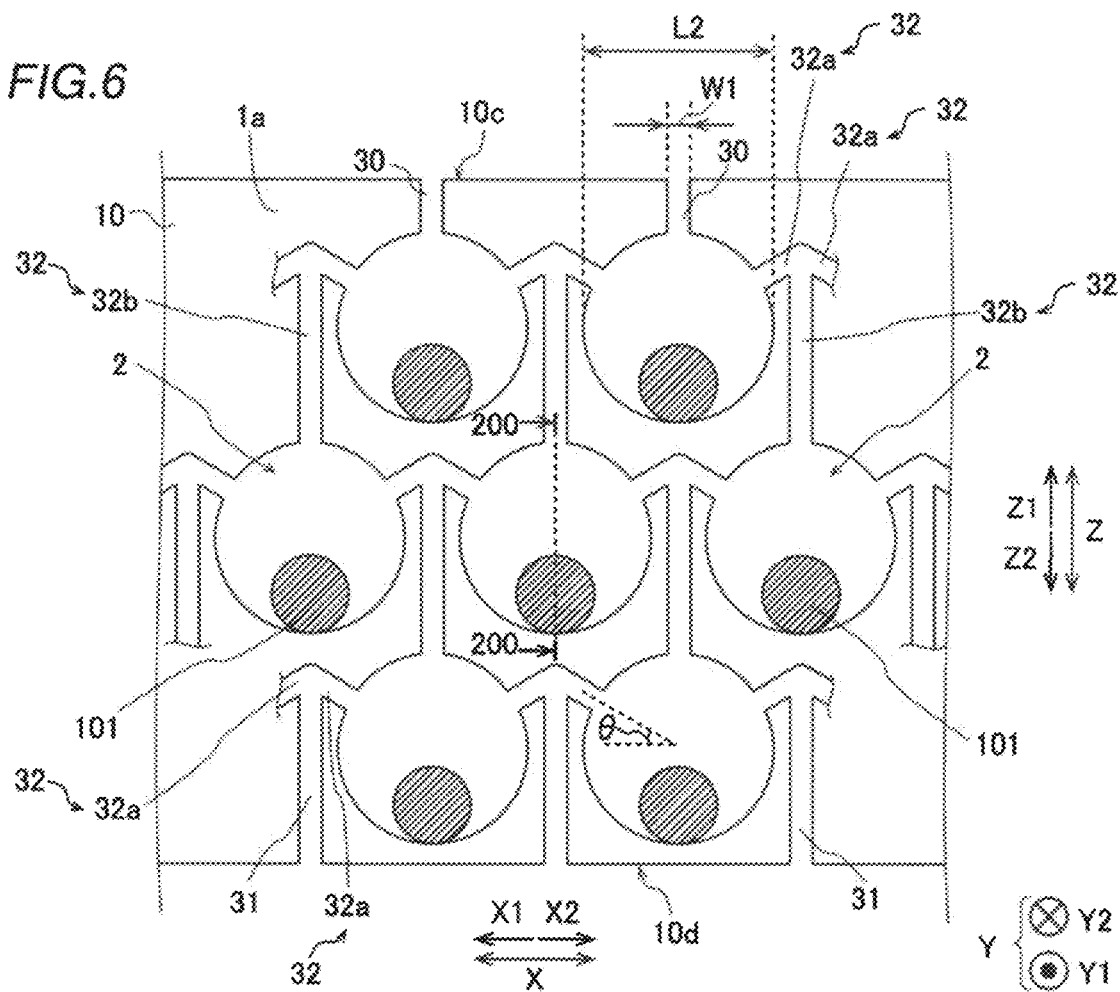
FIG. 6 is a schematic view showing the positional relationship between the wells and the culture solution conduits in the cell culture device according to the first to third embodiments.

In the first embodiment, as shown in FIG. 6, in a state in which the tape 10 circumferentially wound is arranged such that the central axis α (see FIG. 5) of the winding is along the vertical direction (Z direction), the culture solution conduits 3 (see FIG. 3) include introduction conduits 30 configured to connect a plurality of wells 2 (a plurality of wells 2 arranged at the topmost level) arranged at an end 10*c* on the upper side (Z1 direction side) of the tape 10 and in the vicinity of the end 10*c* and adjusted for the culture solution to be introduced thereinto. The culture solution conduits 3 also include discharge conduits 31 configured to connect a plurality of wells 2 (a plurality of wells 2 arranged at the bottommost level) arranged at an end 10*d* on the lower side (Z2 direction side) of the tape 10 and in the vicinity of the end 10*d* and adjusted for the culture solution to be discharged therethrough. Furthermore, the culture solution conduits 3 include connection conduits 32 configured to connect the plurality of wells 2 to each other. FIG. 6 illustrates that only three wells 2 are arranged in the Z direction for simplification, but actually three or more wells 2 are arranged.

Specifically, the introduction conduits 30 extend in the Z direction between the end 10*c* of the tape 10 and the plurality of wells 2 in the vicinity of the end 10*c*. An introduction conduit 30 is provided for each topmost well 2. The connection conduits 32 include connection conduit portions 32*a* that connect wells 2 adjacent to each other in a direction (X direction in FIG. 6) orthogonal to the Z direction on the inner circumferential surface 1*a*. Each of the wells 2 is connected to a connection conduit portion 32*a* that extends toward a well 2 on the X1 direction side and a connection conduit portion 32*a* that extends toward a well 2 on the X2 direction side.

The connection conduit portion 32*a* that extends from the well 2 on the X1 direction side to the well 2 on the X2 direction side and the connection conduit portion 32*a* that extends from the well 2 on the X2 direction side to the well 2 on the X1 direction side are connected to each other between two wells 2 adjacent to each other in the X direction.

A discharge conduit 31 is provided for each bottommost well 2. Specifically, the discharge conduit 31 extends in the Z direction between the bottommost wells 2 adjacent to each other in the X direction. Furthermore, the discharge conduit 31 is connected to a portion at which the connection conduit portions 32*a* are connected to each other between the adjacent bottommost wells 2.

In the first embodiment, the plurality of wells 2 are provided in a staggered manner on the inner circumferential surface 1*a* of the tape 10. The connection conduits 32 include connection conduit portions 32*b* that connect the connection conduit portions 32*a* that connect the wells 2 adjacent to each other in the X direction to wells 2 arranged on the lower side (Z2 direction side) of the connection conduit portions 32*a*. The connection conduit portions 32*b* extend in the Z direction. Note that the culture solution is introduced into the wells 2 from the connection conduit portions 32*b* (the introduction conduits 30 in the wells 2 in the vicinity of the end 10*c*), and is discharged from the wells 2 via the connection conduit portions 32*a*. The culture solution discharged via the connection conduit portions 32*a* flows into the connection conduit portions 32*b* (the discharge conduits 31 in the wells 2 in the vicinity of the end 10*d*), and then is introduced into lower wells 2.

The connection conduits 32 are configured to connect portions of the plurality of wells 2 on the upper side (Z1 direction side) to each other in a state in which the tape 10 circumferentially wound is arranged such that the central axis α of the winding is along the vertical direction (Z direction). Specifically, the connection conduit portions 32*b* are connected to ends of the wells 2 on the Z1 direction side. Two connection conduit portions 32*a* are connected to the upper sides (Z1 direction sides) of the centers of the wells 2.

The introduction conduits 30 are connected to upper portions of the plurality of wells 2 arranged in the vicinity of the end 10*c* (the plurality of wells 2 arranged at the topmost level) in a state in which the tape 10 circumferentially wound is arranged such that the central axis α of the winding is along the vertical direction (Z direction). Specifically, the introduction conduits 30 are connected to the ends on the Z1 direction side of the plurality of wells 2 arranged in the vicinity of the end 10*c* (the plurality of wells 2 arranged at the topmost level).

The discharge conduits 31 are configured to be connected to upper portions of the plurality of wells 2 arranged in the vicinity of the lower end 10*d* (the plurality of wells 2 arranged at the bottommost level) via the connection conduits 32. Specifically, the discharge conduits 31 are connected to the upper portions of the wells 2 via the connection conduit portions 32*a*.

In the first embodiment, the connection conduits 32 are inclined upward from the upper portions of the plurality of wells 2 toward the adjacent wells 2 in a state in which the tape 10 circumferentially wound is arranged such that the central axis α of the winding is along the vertical direction (Z direction).

Specifically, the connection conduit portions 32*a* that extend from the wells 2 on the X1 direction side toward the wells 2 on the X2 direction side among the wells 2 adjacent to each other in the X direction are inclined (see FIG. 6) upward (Z1 direction) in an X2 direction.

The connection conduit portions 32*a* that extend from the wells 2 on the X2 direction side toward the wells 2 on the X1 direction side among the wells 2 adjacent to each other in the X direction are inclined (see FIG. 6) upward (Z1 direction) in the X1 direction.

That is, the connection conduit portions 32*a* that extend upward (Z1 direction) from the wells 2 on the X1 direction side toward the wells 2 on the X2 direction side and the connection conduit portions 32*a* that extend upward (Z1 direction) from the wells 2 on the X2 direction side toward the wells 2 on the X1 direction side are connected such that inverted V-shaped conduits are formed between the wells 2 adjacent in the X direction. An angle (tilt angle) e between the connection conduit portion 32*a* and the X direction is 0 degrees or more and 90 degrees or less, and is 30 degrees, for example.

When the inner circumferential surface 1*a* is viewed from the front side (viewed from the Y1 direction side), the wells 2 each have a substantially circular shape. However, the present invention is not limited to this, but the wells 2 each may have a substantially polygonal shape when the inner circumferential surface 1*a* is viewed from the front side. The diameter of each of the wells 2 has a length L2 (several hundreds of micrometers, for example). When the inner circumferential surface 1*a* is viewed from the front side, the width of each of the culture solution conduits 3 (the introduction conduits 30, the discharge conduits 31, the connection conduit portions 32*a*, and the connection conduit portions 32*b*) in a direction orthogonal to a direction in which the culture solution flows is W1 (several tens of micrometers, for example).

Figure 7:
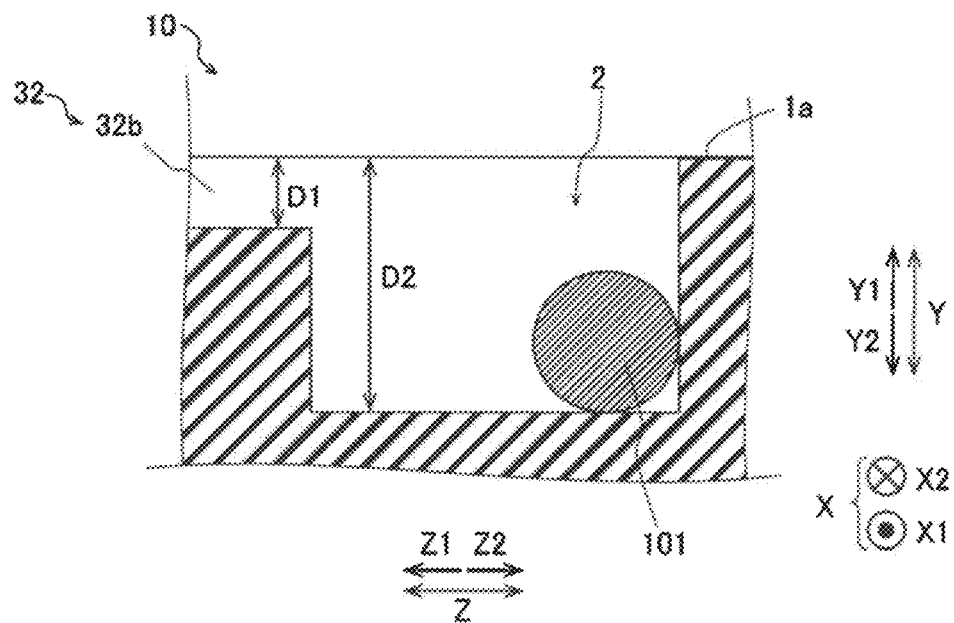
FIG. 7 is a sectional view taken along the line 200-200 in FIG. 6.

As shown in FIG. 7, the depth of each of the culture solution conduits 3 (FIG. 7 shows the connection conduit portion 32*b* as an example) in a Y direction is D1. The depth of each of the plurality of wells 2 in the Y direction is D2. The depth D2 is larger than the depth D1. In this case, the flow rate of the culture solution can be reduced as compared with a case in which the depth D2 is equal to or less than the depth D1. Thus, destruction of the cells 101 (melting of a cellular mass) due to the pressure of the flow of the culture solution can be significantly reduced or prevented. Note that it is also possible to increase the depth D1 and the width W1 (see FIG. 6) to increase the flow rate of the culture solution and shorten the time required for culture with the culture solution. FIG. 7 shows an example in which the diameter of each of the wells 2 does not change in the depth direction, but the present invention is not limited to this. The diameter of each of the wells 2 may increase toward the inner circumferential surface 1a side.

Figure 8:
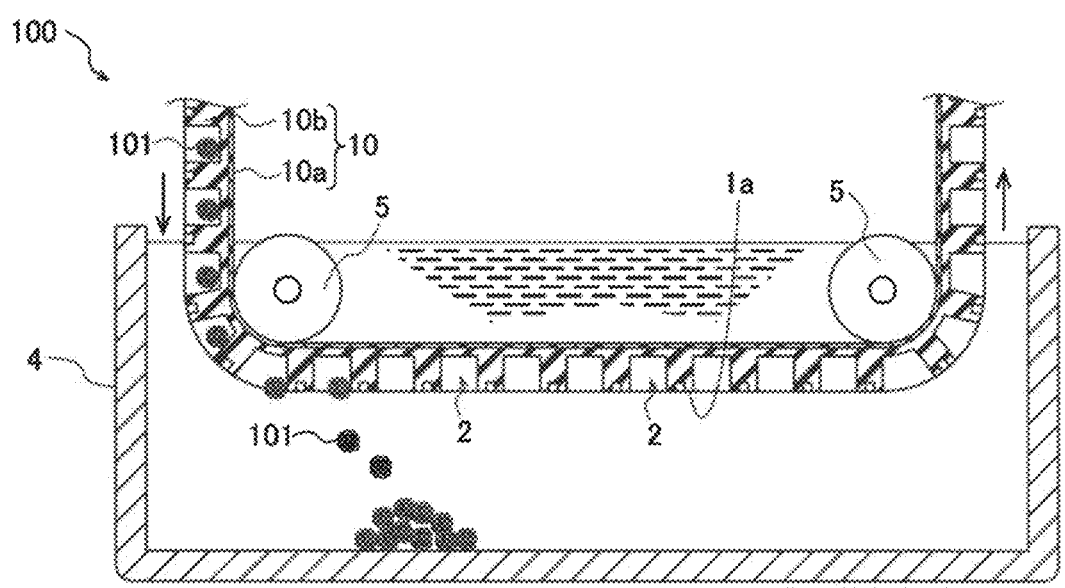
FIG. 8 is a diagram for illustrating a cell collection method in the cell culture device according to the first embodiment.

Collection of the cells 101 is now described with reference to FIG. 8. As shown in FIG. 8, the cell culture device 100 includes a collection container 4 in which the culture solution is stored. In addition, the cell culture device 100 includes an unwinding device 5 that unwinds the tape 10 circumferentially wound. The unwinding device 5 is configured to unwind the tape 10 at a constant speed. The culture solution stored in the collection container 4 is an example of a "solution" in the claims.

In the first embodiment, the cell culture device 100 is configured to collect the cells 101 contained in the wells 2 while allowing the unwound tape 10 to pass through the culture solution stored in the collection container 4. Specifically, the unwinding device 5 of the cell culture device 100 is configured to pull out the tape 10, which has passed through the culture solution, from the culture solution after allowing the unwound tape 10 to pass through the culture solution in the collection container 4.

The tape 10 is unwound such that the openings 2a (see FIG. 3) of the plurality of wells 2 face downward. The collection container 4 is configured to collect, from the plurality of wells 2 of the tape 10 that passes through the culture solution while the openings 2a of the plurality of wells 2 face downward, the cells 101 that settle in the culture solution due to their own weights. That is, the cells 101 that settle from the plurality of wells 2 are accumulated at the bottom of the collection container 4.

Figure 9:
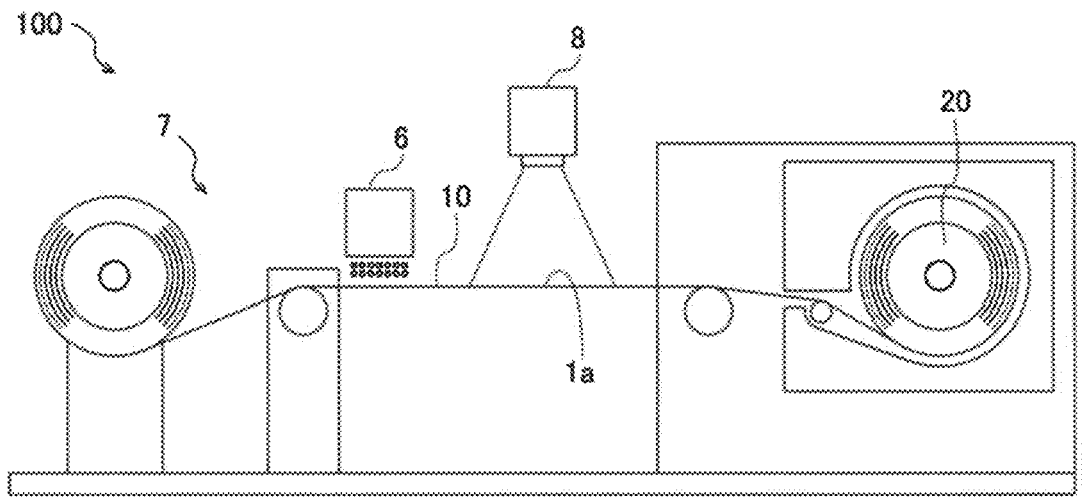
FIG. 9 is a diagram for illustrating a cell seeding method in the cell culture device according to the first embodiment.

Seeding of the cells 101 is now described with reference to FIG. 9. The cell culture device 100 includes a cell suspension injector 6 that sprays a cell suspension containing the cells 101 toward the inner circumferential surface 1a of the tape 10. Furthermore, the cell culture device 100 includes a winding device 7 that winds the tape 10. The tape 10 passes below the cell suspension injector 6 while being wound by the winding device 7. Furthermore, the tape 10 is wound such that the openings 2a (see FIG. 3) of the plurality of wells 2 face upward (to the cell suspension injector 6 side). The cell suspension injector 6 sprays the cell suspension into the wells 2 that pass below the cell suspension injector 6 such that the cells 101 are seeded in the wells 2. A camera 8 is provided in the cell culture device 100. It is possible to confirm, by an image captured by the camera 8, whether or not the cell suspension has been properly injected into the wells 2 by the cell suspension injector 6.

A cell culture method according to the first embodiment is now described with reference to a flowchart of FIG. 10.

Figure 10:
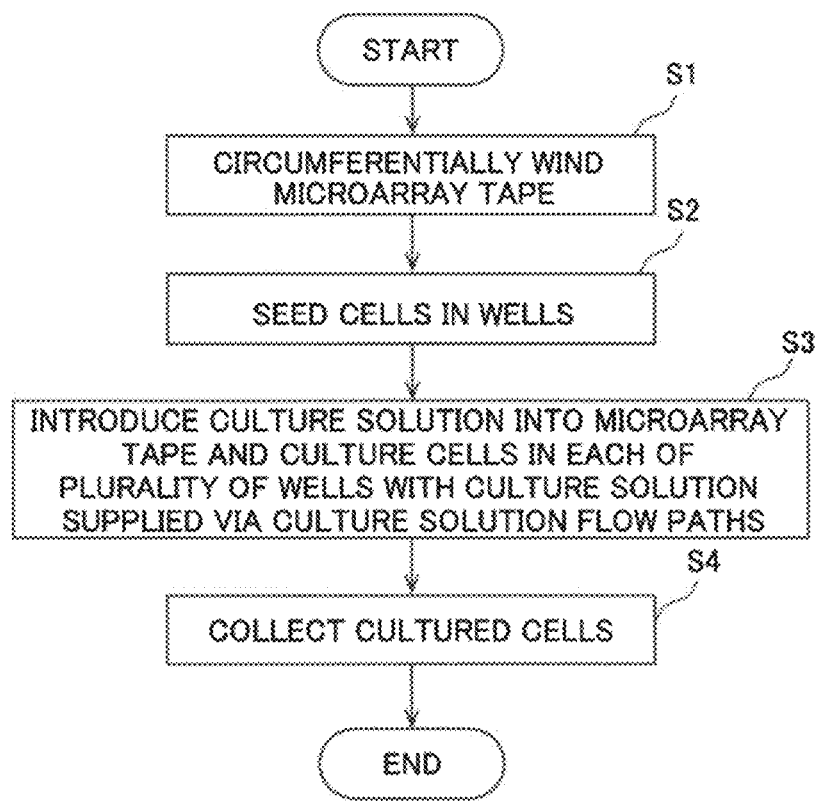
FIG. 10 is a flowchart for illustrating a cell culture method in the cell culture device according to the first embodiment.

As shown in FIG. 10, in the cell culture method according to the first embodiment, in step S1, the band-shaped tape 10 is circumferentially wound. Then, in step S2, while the tape 10 is wound, the cell suspension is sprayed onto the inner circumferential surface 1a of the tape 10, and the cells 101 are seeded in the plurality of wells 2. Then, in step S3, the culture solution is introduced from the upper side of the tape 10 with the central axis α of the winding of the tape 10 circumferentially wound being along the vertical direction.

Thus, the culture solution is supplied to the cells 101 seeded in the plurality of wells 2 via the culture solution conduits 3, and the cells 101 are cultured. Then, in step S4, the tape 10 circumferentially wound passes through the culture solution in the collection container 4 while the openings 2a of the plurality of wells 2 face downward. Thus, the cells 101 in the wells 2 settle in the culture solution in the collection container 4 and are collected.

Advantages of First Embodiment

According to the first embodiment, the following advantages are obtained.

According to the first embodiment, as described above, the cell culture device 100 includes the flexible tape 10 configured to be circumferentially windable. Furthermore, the tape 10 has the inner circumferential surface 1a provided with the plurality of concave wells 2 adjusted for the cells 101 to be cultured therein, and at least some of the plurality of wells 2 are connected to each other by the culture solution conduits 3 adjusted for a culture solution to flow therethrough. Accordingly, the cells 101 can be seeded in each of the plurality of wells 2 having a concave shape, and the cells 101 seeded in each of the plurality of wells 2 can be cultured by the culture solution that flows through the culture solution conduits 3. The number (or amount) of cells 101 to be cultured is determined according to the sizes of the wells 2, and thus the number of cells 101 to be cultured in each of the plurality of wells 2 can be uniform when the size of each of the plurality of wells is uniform. Consequently, a variation in the density of the cells 101 seeded and cultured on the inner circumferential surface 1a can be significantly reduced or prevented. Thus, a uniform density of the seeded (cultured) cells 101 can be achieved while a large number of cells 101 are seeded (cultured) on the inner circumferential surface 1a of the tape 10.

According to the first embodiment, as described above, in the cell culture device 100, in a state in which the tape 10 is circumferentially wound, the plurality of wells 2 and the culture solution conduits 3 are provided on the inner circumferential surface 1a of the tape 10 and are covered by the outer circumferential surface 1b of the tape 10 wound on the inner circumferential side of the plurality of wells 2 and the culture solution conduits 3. Accordingly, the outer circumferential surface 1b of the tape 10 wound on the inner circumferential side can cover (seal) the plurality of wells 2 and the culture solution conduits 3, and thus leakage of the culture solution from the wells 2 and the culture solution conduits 3 can be significantly reduced or prevented. Furthermore, an increase in the number of components can be significantly reduced or prevented as compared with a case in which a member separate from the tape 10 is used to cover the plurality of wells 2 and the culture solution conduits 3.

According to the first embodiment, as described above, in the cell culture device 100, the plurality of wells 2 and the culture solution conduits 3 are not provided on the inner circumferential surface 1a of the tape 10 wound on the innermost circumference of the tape 10 circumferentially wound, and are provided on the inner circumferential surface 1a of the tape 10 wound on the outer circumferential side of the tape 10 wound on the innermost circumference. Accordingly, the plurality of wells 2 and the culture solution conduits 3 are not provided on the inner circumferential surface 1a of the tape 10 wound on the innermost circumference, and thus the culture solution does not flow on the inner circumferential surface 1a of the tape 10 wound on the innermost circumference. The tape 10 is not provided on the inner circumferential side of the tape 10 wound on the innermost circumference, and thus when the plurality of wells 2 and the culture solution conduits 3 are provided on the inner circumferential surface 1a of the tape 10 on the innermost circumference, the wells 2 and the culture solution conduits 3 on the inner circumferential surface 1a of the tape 10 on the innermost circumference are not covered by the tape 10 from the inner circumferential side. In this case, the culture solution may leak from the inner circumferential surface 1a of the tape 10 on the innermost circumference. Therefore, the plurality of wells 2 and the culture solution conduits 3 are not provided on the inner circumferential surface 1a of the tape 10 on the innermost circumference, and thus the culture solution can be prevented from leaking from the inner circumferential surface 1a of the tape 10 on the innermost circumference.

According to the first embodiment, as described above, in the cell culture device 100, in a state in which the tape 10 circumferentially wound is arranged such that the central axis α of the winding is along the vertical direction, the culture solution conduits 3 include the introduction conduits 30 configured to connect the plurality of wells 2 arranged at the upper end 10c of the tape 10 and in the vicinity of the upper end 10c and adjusted for the culture solution to be introduced thereinto, the discharge conduits 31 configured to connect the plurality of wells 2 arranged at the lower end 10d of the tape 10 and in the vicinity of the lower end 10d and adjusted for the culture solution to be discharged therethrough, and the connection conduits 32 configured to connect the plurality of wells 2 to each other. Accordingly, the culture solution can be easily introduced into the wells 2 arranged in the vicinity of the upper end 10c of the tape 10 through the introduction conduits 30, and the culture solution can be easily discharged from the wells 2 arranged in the vicinity of the lower end 10d of the tape 10 through the discharge conduits 31. Furthermore, the introduced culture solution can easily flow into each of the plurality of wells 2 through the connection conduits 32.

According to the first embodiment, as described above, in the cell culture device 100, the connection conduits 32 connect the upper portions of the plurality of wells 2 to each other in a state in which the tape 10 circumferentially wound is arranged such that the central axis α of the winding is along the vertical direction. Accordingly, the culture solution flows downward from above during culturing of the cells 101, and thus unlike a case in which the connection conduits 32 connect lower portions of the plurality of wells 2 to each other, discharge of the cells 101 contained in the wells 2 from the wells 2 due to the downward flow of the culture solution can be significantly reduced or prevented.

According to the first embodiment, as described above, in the cell culture device 100, in a state in which the tape 10 circumferentially wound is arranged such that the central axis α of the winding is along the vertical direction, the introduction conduits 30 are connected to the upper portions of the plurality of wells 2 arranged in the vicinity of the upper end 10c, and the discharge conduits 31 are connected to the upper portions of the plurality of wells 2 arranged in the vicinity of the lower end 10d via the connection conduits 32. Accordingly, both the introduction conduits 30 and the discharge conduits 31 are connected to the upper portions of the wells 2, and thus discharge of the cells 101 contained in the plurality of wells 2 arranged in the vicinity of the upper end 10c of the tape 10 and the plurality of wells 2 arranged in the vicinity of the lower end 10d of the tape 10 from the wells via the connection conduits 32 due to the flow of the culture solution can be significantly reduced or prevented.

According to the first embodiment, as described above, in the cell culture device 100, the connection conduits 32 are inclined upward from the upper portions of the plurality of wells 2 toward the adjacent wells 2 in a state in which the tape 10 circumferentially wound is arranged such that the central axis x of the winding is along the vertical direction. Accordingly, a force acts downward on the cells 101 due to their own weights, and thus as compared with a case in which the connection conduits 32 are inclined downward from the wells 2, discharge of the cells 101 contained in the wells 2 from the wells 2 via the connection conduits 32 can be effectively significantly reduced or prevented.

According to the first embodiment, as described above, in the cell culture device 100, the plurality of wells 2 are provided in a staggered manner on the inner circumferential surface 1a of the tape 10. Accordingly, as compared with a case in which the plurality of wells 2 are provided in a matrix, the plurality of wells 2 can be densely arranged on the inner circumferential surface 1a of the tape 10. Consequently, the sizes of the wells 2 can be easily increased. Moreover, the number of wells 2 can be easily increased.

According to the first embodiment, as described above, in the cell culture device 100, the inner circumferential surface 1a of the tape 10 provided with the plurality of wells 2 is non-adhesive to the cells 101. Accordingly, it becomes difficult for the cells 101 to adhere to the wells 2, and thus the cells 101 can easily adhere (or adsorb) to each other in the wells 2. Consequently, a mass of the cells 101 (i.e., a cell clump) can be easily formed.

According to the first embodiment, as described above, the cell culture device 100 includes the collection container 4 configured to store the culture solution through which the tape 10 unwound from the circumferentially wound state passes and to collect the cells 101 contained in the wells 2 of the tape 10 that passes through the culture solution. Accordingly, the cells 101 can be collected while exposure of the cultured cells 101 to the air is significantly reduced or prevented.

According to the first embodiment, as described above, in the cell culture device 100, the collection container 4 collects, from the plurality of wells 2 of the tape 10 that passes through the culture solution while the openings 2a of the plurality of wells 2 face downward, the cells 101 that settle in the culture solution due to their own weights. Accordingly, the cells 101 can be collected by settling due to their own weights, and thus it is not necessary to use a dedicated member for carrying the cells 101 to the collection container 4. Consequently, an increase in the number of components can be significantly reduced or prevented in collecting the cells 101.

According to the first embodiment, as described above, the cell culture method includes seeding the cells 101 in each of the plurality of wells 2 of the tape 10 and circumferentially winding the tape 10 after seeding the cells 101. The cell culture method further includes flowing the culture solution from the upper side of the tape 10 circumferentially wound into each of the plurality of wells 2 via the culture solution conduits 3 in a state in which the tape 10 circumferentially wound is arranged such that the central axis α of the winding is along the vertical direction after circumferentially winding the tape 10. Accordingly, the cells 101 can be seeded in each of the plurality of concave wells 2, and the cells 101 seeded in each of the plurality of wells 2 can be cultured by the culture solution that flows through the culture solution conduits 3.

According to the first embodiment, as described above, the cell culture method includes unwinding the tape 10 circumferentially wound and collecting the cells 101 contained in the wells 2 while passing the unwound tape 10 through the culture solution stored in the collection container 4 after culturing the cells 101. Accordingly, exposure of the cells 101 to the air during collection of the cultured cells 101 can be significantly reduced or prevented. Consequently, deterioration of the cells 101 during collection of the cells 101 can be significantly reduced or prevented.

Second Embodiment

The configuration of a cell culture device 300 according to a second embodiment is now described with reference to FIGS. 12 and 13. The cell culture device 300 according to the second embodiment is configured to suction and collect cells 101 contained in wells 2 from the upper side, unlike the cell culture device 100 according to the first embodiment configured to settle, in the collection container 4, the cells 101 contained in the wells 2 and collect the cells 101. The same or similar configurations as those of the first embodiment are denoted by the same reference numerals, and description thereof is omitted.

(Configuration of Cell Culture Device)

Figure 12:
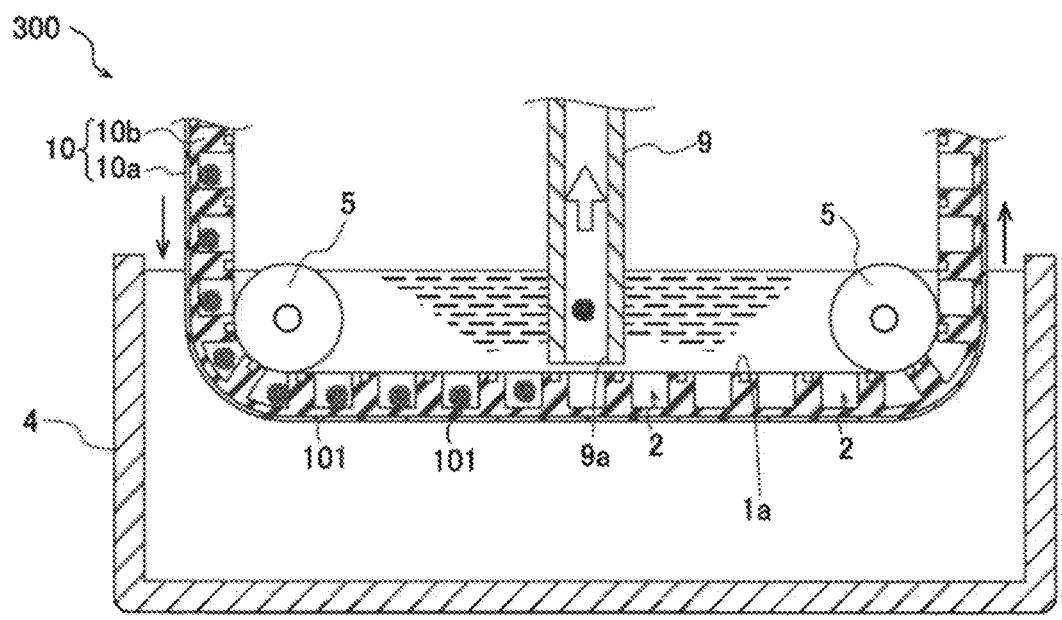
FIG. 12 is a diagram for illustrating a cell collection method in the cell culture device according to the second embodiment.

In the second embodiment, as shown in FIG. 12, a tape 10 is unwound such that openings 2a (see FIG. 3) of a plurality of wells 2 face upward. The cell culture device 300 includes a cell suction nozzle 9 that picks the cells 101 from the plurality of wells 2 of the tape 10 that passes through a culture solution in a collection container 4 while the openings 2a of the plurality of wells 2 face upward. Specifically, the cell suction nozzle 9 is configured to suction the cells 101 from the wells 2 of the tape 10 that passes through the culture solution in the collection container 4 below the cell suction nozzle 9. The cell suction nozzle 9 is an example of a "first cell picking unit" or a "cell suction unit" in the claims.

That is, the cells 101 contained in the wells 2 are suctioned upward by the cell suction nozzle 9. In this case, the cells 101 are suctioned into the cell suction nozzle 9 via an opening 9a of the cell suction nozzle 9. When the cell suction nozzle 9 is viewed from below, the opening 9a has a rectangular shape (see FIG. 13).

Figure 13:
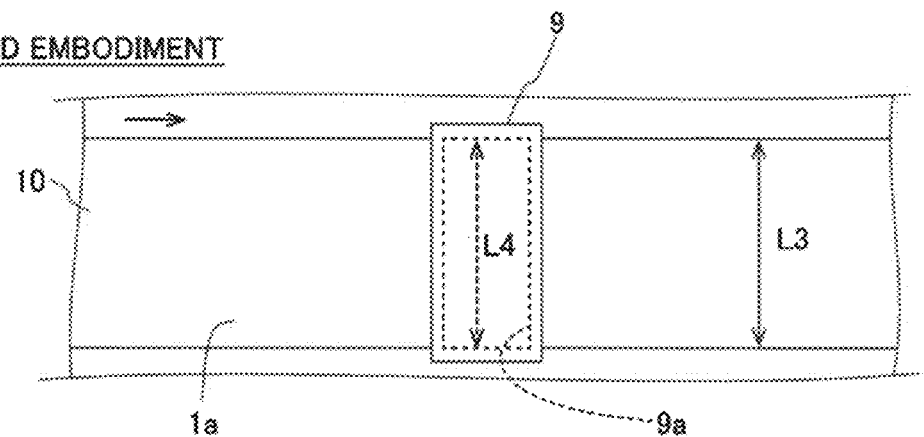
FIG. 13 is a plan view of a cell suction nozzle of the cell culture device according to the second embodiment, as viewed from above.

As shown in FIG. 13, in the width direction (a vertical direction in FIG. 13) of the tape 10, the opening 9a of the cell suction nozzle 9 has a length L4 (a length substantially equal to the length L3, for example) corresponding to the length L3 of the tape 10 in the width direction. Thus, all of the plurality of wells 2 pass below the cell suction nozzle 9, and thus all of the cells 101 contained in the wells 2 can be suctioned. As long as all of the plurality of wells 2 pass below the cell suction nozzle 9, the length L4 of the opening 9a may be larger (smaller) than the length L3 of the tape 10. In FIG. 13, the wells 2 and the culture solution conduits 3 are not shown for simplification.

The remaining configurations of the second embodiment are similar to those of the first embodiment.

Advantages of Second Embodiment

According to the second embodiment, the following advantages are obtained.

According to the second embodiment, as described above, the cell culture device 300 includes the cell suction nozzle 9 configured to pick the cells 101 from the plurality of wells 2 of the tape 10 that passes through the culture solution while the openings 2a of the plurality of wells 2 face upward. Accordingly, the cells 101 can be collected more reliably by the cell suction nozzle 9 as compared with a case in which the cells 101 settle downward due to their own weights and are collected. Furthermore, damage and deterioration of the cells 101 can be significantly reduced or prevented as compared with a case in which the cells 101 are directly picked by an instrument.

The remaining advantages of the second embodiment are similar to those of the first embodiment.

Third Embodiment

The configuration of a cell culture device 500 according to a third embodiment is now described with reference to FIGS. 2, 9, 12, and 14 to 19. The cell culture device 500 according to the third embodiment is configured to wind a tape 10 by a core 50 and a core 60 in a housing 40 without using a winding device 7, unlike the cell culture device 100 according to the first embodiment configured to wind the tape 10 by the winding device 7. The same or similar configurations as those of the first embodiment are denoted by the same reference numerals, and description thereof is omitted.

(Configuration of Cell Culture Device)

Figure 14:
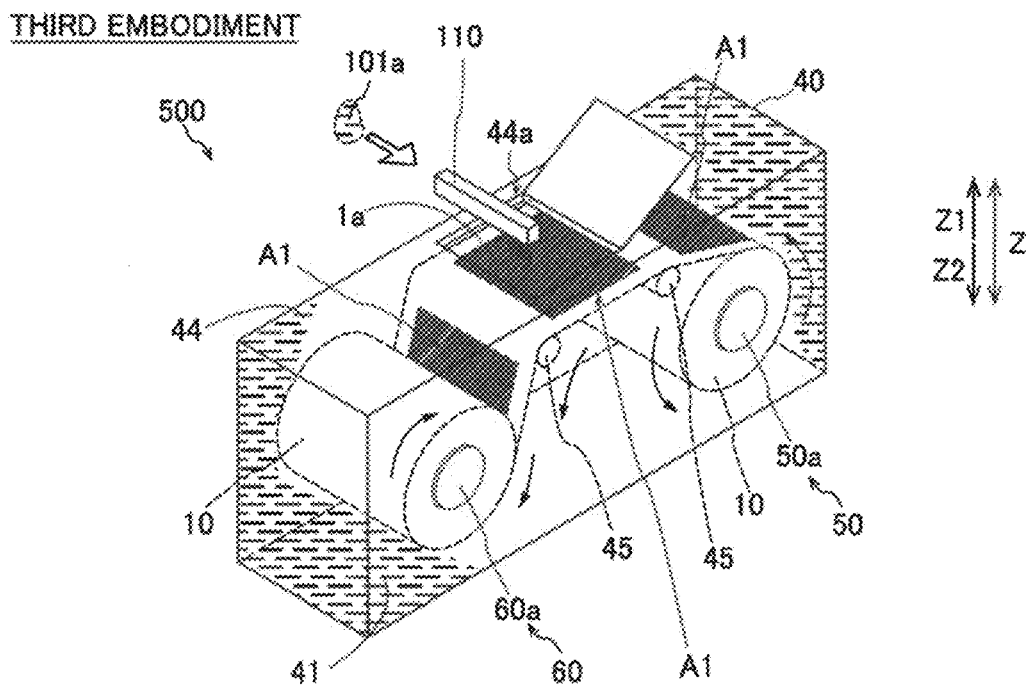
FIG. 14 is a perspective view of the cell culture device according to the third embodiment at the time of cell introduction.

As shown in FIG. 14, the cell culture device 500 includes the housing 40. The housing 40 has a substantially rectangular parallelepiped shape. The housing 40 is made of a resin, for example.

The housing 40 houses the tape 10. Furthermore, the cell culture device 500 includes the core 50 that extends along the central axis α1 (see FIG. 15) of a winding of the tape 10. At least a portion of the core 50 is housed in the housing 40. Specifically, a core body 50c (see FIG. 15) of the core 50 is housed in the housing 40. The core body 50c is a portion of the core 50 other than protruding ends 50a and 50b (see FIG. 15) that protrude to the outside of the housing 40. The protruding end 50b is provided on a side opposite to the protruding end 50a. The core 50 is an example of a "second core" or a "first side core" in the claims.

The cell culture device 500 also includes the core 60 that extends along the central axis α2 (see FIG. 15) of the winding of the tape 10. The core 60 is provided separately from the core 50. Furthermore, the central axis α1 of the core 50 and the central axis α2 of the core 60 extend substantially parallel to each other. The core 60 is an example of a "third core" or a "second side core" in the claims.

At least a portion of the core 60 is housed in the housing 40. Specifically, a core body 60c (see FIG. 15) of the core 60 is housed in the housing 40. The core body 60c is a portion of the core 60 other than protruding ends 60a and 60b (see FIG. 15) that protrude to the outside of the housing 40. The protruding end 60b is provided on a side opposite to the protruding end 60a.

The core 60 is adjusted for the tape 10 unwound from the core 50 to be wound therearound. Furthermore, the core 50 is adjusted for the tape 10 unwound from the core 60 to be wound therearound.

Figure 15:
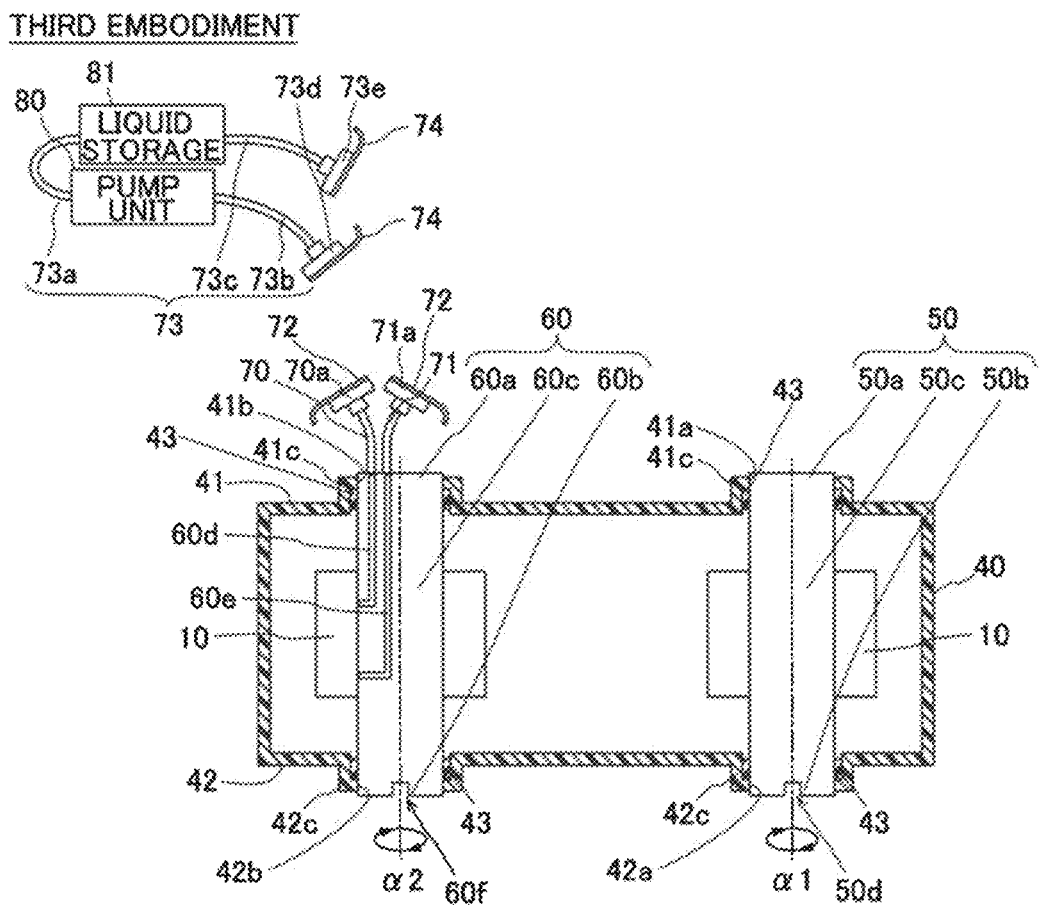
FIG. 15 is a sectional view of the cell culture device according to the third embodiment at the time of tape winding.
Figure 17:
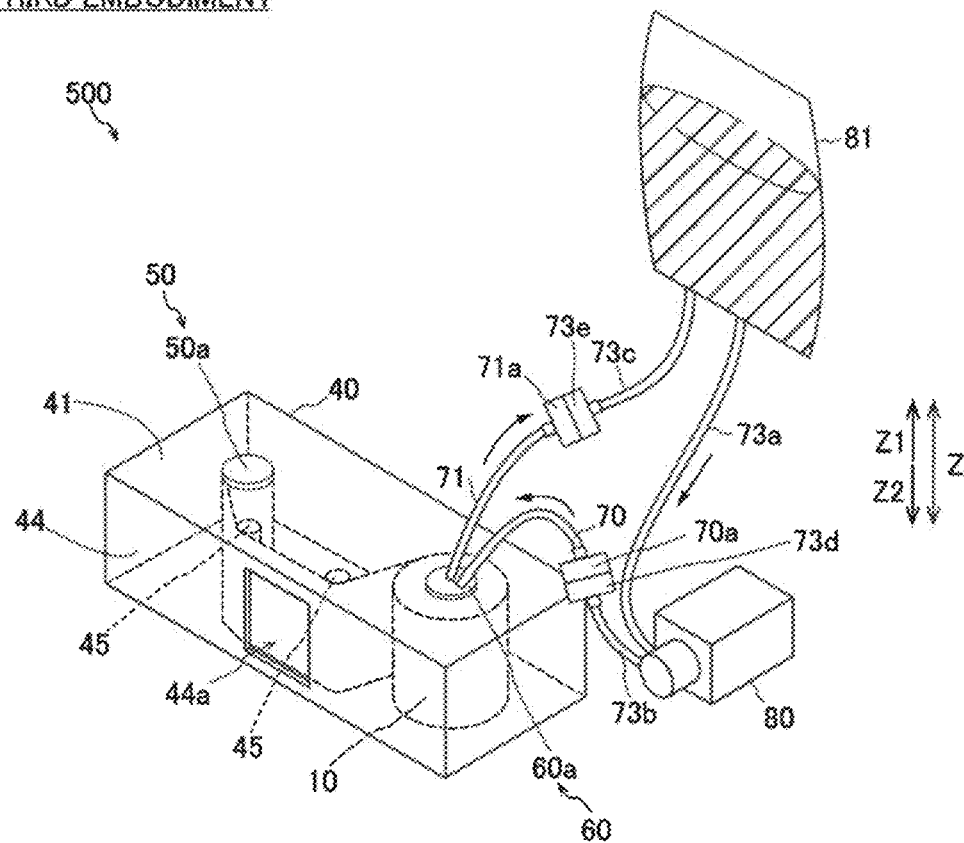
FIG. 17 is a perspective view of the cell culture device according to the third embodiment at the time of culture solution introduction.
Figure 18:
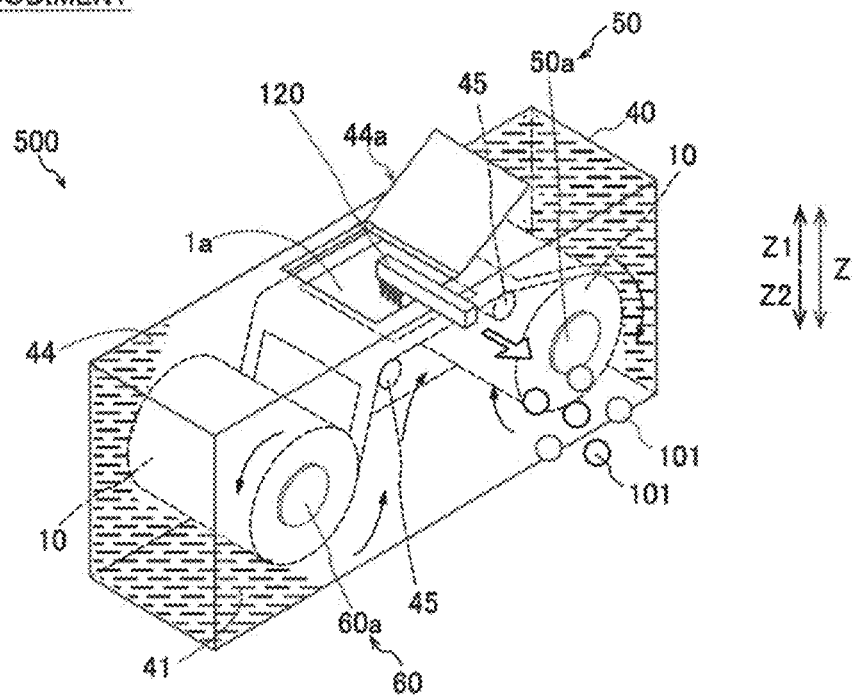
FIG. 18 is a perspective view of the cell culture device according to the third embodiment at the time of cell picking.

As shown in FIG. 15, the housing 40 includes an opening 41a and an opening 41b provided on a side surface 41 in a direction in which the central axis α1 (α2) extends. Furthermore, the housing 40 includes protrusions 41c that protrude to the outside (the upper side in FIG. 15) of the housing 40. Two protrusions 41c are provided on the side surface 41. The opening 41a is arranged on one of the two protrusions 41c, and the opening 41b is arranged on the other of the two protrusions 41c. In FIGS. 14, 17, and 18, the protrusions 41c are not shown for simplification.

The housing 40 includes an opening 42a and an opening 42b provided on a side surface 42 in the direction in which the central axis α1 (α2) extends. Furthermore, the housing 40 includes protrusions 42c that protrude to the outside (the lower side in FIG. 15) of the housing 40. Two protrusions 42c are provided on the side surface 42. The opening 42a is arranged on one of the two protrusions 42c, and the opening 42b is arranged on the other of the two protrusions 42c. The side surface 41 and the side surface 42 face each other.

The protruding end 50a of the core 50 protrudes to the outside of the housing 40 via the opening 41a of the housing 40. The protruding end 50b of the core 50 protrudes to the outside of the housing 40 via the opening 42a of the housing 40.

The protruding end 60a of the core 60 protrudes to the outside of the housing 40 via the opening 41b of the housing 40. The protruding end 60b of the core 60 protrudes to the outside of the housing 40 via the opening 42b of the housing 40.

The cell culture device 500 also includes a tube 70 connected to a conduit 60d of the protruding end 60a of the core 60. The tube 70 is connected to the protruding end 60a so as to introduce a culture solution into the tape 10 via the conduit 60d. The cell culture device 500 also includes a tube 71 connected to a conduit 60e of the protruding end 60a of the core 60. The tube 71 is connected to the protruding end 60a so as to suction the culture solution from the conduit 60e. That is, the tube 70 and the tube 71 are connected to the protruding end 60a on the outside of the housing 40.

The cell culture device 500 also includes an aseptic connector 70a that separates and connects a first side portion 73b of a tube 73 described below and the tube 70. The cell culture device 500 also includes an aseptic connector 71a that separates and connects a second side portion 73c of the tube 73 described below and the tube 71. Specifically, the aseptic connector 70a is provided at an end of the tube 70 opposite to the protruding end 60a. The aseptic connector 71a is provided at an end of the tube 71 opposite to the protruding end 60a. A cap 72 is attached to each of the aseptic connectors 70a and 71a to prevent contamination of bacteria, for example, when the aseptic connectors 70a and 71a are separated from the tube 73 described below.

The cell culture device 500 also includes a pump unit 80 that delivers the culture solution. The cell culture device 500 also includes a liquid storage 81 that stores the culture solution.

The cell culture device 500 also includes the tube 73. The tube 73 includes an intermediate portion 73a that connects the pump unit 80 to the liquid storage 81. The tube 73 also includes the first side portion 73b that extends from the pump unit 80. The tube 73 further includes the second side portion 73c that extends from the liquid storage 81.

The cell culture device 500 also includes an aseptic connector 73d that separates and connects the first side portion 73b of the tube 73 and the tube 70. The cell culture device 500 also includes an aseptic connector 73e that separates and connects the second side portion 73c of the tube 73 and the tube 71. Specifically, the aseptic connector 73d is provided at an end of the first side portion 73b of the tube 73 opposite to the pump unit 80. The aseptic connector 73e is provided at an end of the second side portion 73c of the tube 73 opposite to the liquid storage 81. A cap 74 is attached to each of the aseptic connectors 73d and 73e to prevent contamination of bacteria, for example, when the aseptic connectors 73d and 73e are separated from the tubes 70 and 71.

Figure 16:
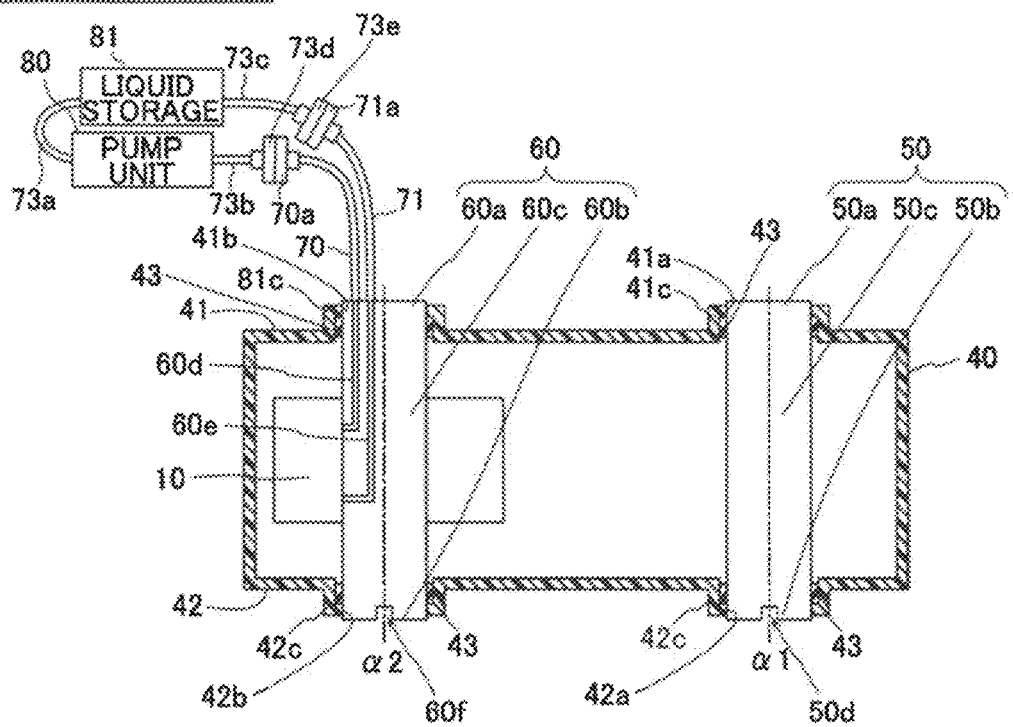
FIG. 16 is a sectional view of the cell culture device according to the third embodiment at the time of culture solution introduction.

That is, the aseptic connector 70a of the tube 70 and the aseptic connector 73d of the first side portion 73b of the tube 73 are separated and connected such that the tube 70 and the tube 73 (first side portion 73b) are separated and connected (see FIG. 16). Furthermore, the aseptic connector 71a of the tube 71 and the aseptic connector 73e of the second side portion 73c of the tube 73 are separated and connected such that the tube 71 and the tube 73 (second side portion 73c) are separated and connected (see FIG. 16). The aseptic connector 70a (aseptic connector 73d) and the aseptic connector 71a (aseptic connector 73e) are used such that it is possible to connect and separate the tubes 70 and 71 and the tube 73 while maintaining airtightness.

An O-ring 43 is provided inward of each of the two protrusions 41c and the two protrusions 42c. The O-ring 43 is provided such that the core 50 (60) rotates while sliding on the inner circumferential surface of the O-ring 43. The O-ring 43 is made of a resin, for example.

In the third embodiment, as shown in FIG. 14, the cell culture device 500 includes a window 44a adjusted for cells 101 to be introduced into the tape 10 being wound around the core 60 from the core 50 inside the housing 40 and adjusted for the cells 101 to be picked from the tape 10 being wound around the core 50 from the core 60 (see FIG. 18) inside the housing 40. Specifically, the window 44a is provided on a side surface 44 of the housing 40 that extends along the direction in which the central axis α1 (α2) (see FIG. 15) extends. The window 44a has a substantially rectangular shape. The window 44a may have a shape (a circular shape, for example) other than the rectangular shape. The window 44a is an example of an "opening" in the claims.

The window 44a is configured to be openable and closable. Specifically, the window 44a is configured to be manually openable and closable. The window 44a may be configured to be automatically openable and closable.

The housing 40 includes guides 45 that guide the tape 10 being wound around the core 50 and the core 60 such that the tape 10 is exposed via the window 44a inside the housing 40. The guide 45 has a rod shape that extends along the direction in which the central axis α1 (α2) extends. Two guides 45 are provided inside the housing 40. The two guides 45 are provided side by side between the core 50 and the core 60. When the core 50 and the core 60 rotate while the tape 10 is guided by the two guides 45, the tape 10 wound around the core 50 is wound around the core 60 (or the tape 10 wound around the core 60 is wound around the core 50).

The two guides 45 are provided along the side surface 44 on which the window 44a is provided. When the side surface 44 is viewed vertically, the window 44a is arranged between the two guides 45. Thus, the tape 10 between the two guides 45 is provided so as to be exposed via the window 44a.

Specifically, when the tape 10 is wound around the core 50 or the core 60 while being guided by the guides 45, the inner circumferential surface 1a of the tape 10 is moved along the window 44a while facing the window 44a. That is, in this case, the window 44a and the inner circumferential surface 1a of the tape 10 overlap each other as viewed in a direction perpendicular to the side surface 44.

The protruding end 50b of the core 50 includes a groove 50d (see FIG. 15) to which a jig (such as a driver) (not shown) for rotating the core 50 is attached. Furthermore, the protruding end 60b of the core 60 includes a groove 60f (see FIG. 15) to which a jig (such as a driver) (not shown) for rotating the core 60 is attached. The tape 10 can be wound around the core 50 (60) by rotating the core 50 (60) by rotating the jig with a motor (not shown), for example. The motors that respectively drive the core 50 and the core 60 are configured to be driven simultaneously. The groove 50*d* may be provided at the protruding end 50*a*.

In the third embodiment, the cell culture device 500 includes a cell suspension injector 110 configured to introduce the cells 101 via the window 44*a* into each of a plurality of wells 2 (see FIG. 2) of the tape 10 being wound around the core 60 from the core 50 while being guided by the guides 45. Specifically, the cell suspension injector 110 is configured to spray a cell suspension 101*a* containing the cells 101 downward (in a Z2 direction in FIG. 14). The configuration of the cell suspension injector 110 is the same or similar as that of the cell suspension injector 6 (see FIG. 9) according to the first embodiment. The cell suspension injector 110 is an example of a "cell introduction unit" in the claims.

The cell culture device 500 includes a cell suction nozzle 120 (see FIG. 18) configured to pick the cells 101 via the window 44*a* from the plurality of wells 2 of the tape 10 being wound around the core 50 from the core 60 while being guided by the guides 45. The cell suction nozzle 120 is configured to suction the cells 101 that move downward (in the Z2 direction in FIG. 18) to the upper side (the Z1 direction side in FIG. 18). The configuration of the cell suction nozzle 120 is the same or similar as that of the cell suction nozzle 9 (see FIG. 12) according to the second embodiment. Instead of the cell suction nozzle 120, a needle (see FIG. 20) for picking cells may be used. The cell suction nozzle 120 is an example of a "second cell picking unit" in the claims.

(Cell Culture Method)

A method for using the cell culture device 400 is now described with reference to FIGS. 14 to 19.

Figure 19:
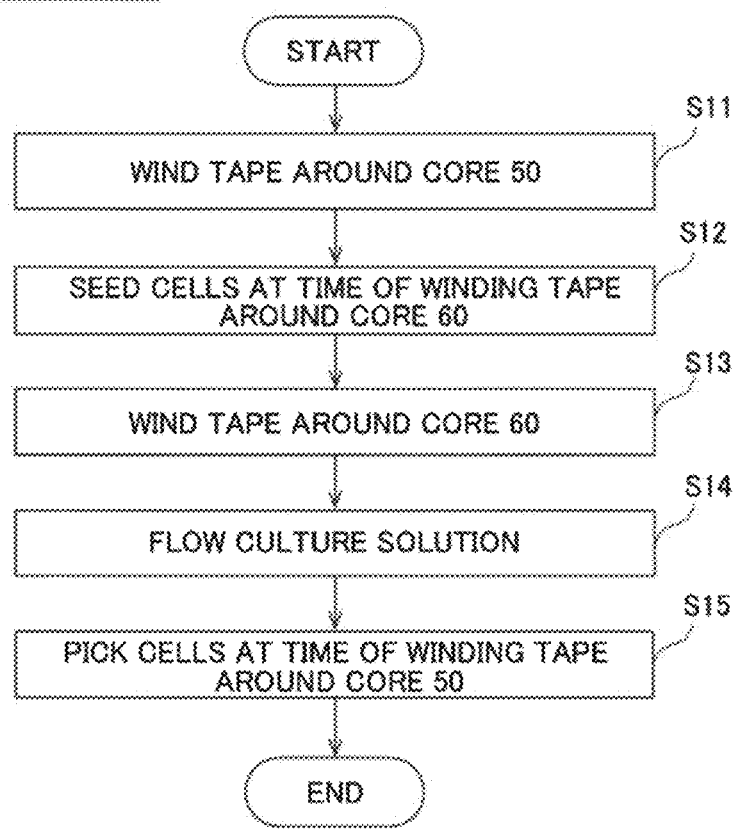
FIG. 19 is a flowchart for illustrating a cell culture method in the cell culture device according to the third embodiment.

First, as shown in FIG. 19, the tape 10 is wound around the core 50 in step S11.

Then, in step S12, the cells 101 are seeded in the wells 2 of the tape 10 when the tape 10 is wound around the core 60. Specifically, first, the tape 10 wound around the core 50 is unwound. Then, the tape 10 unwound from the core 50 is wound around the core 60 while being guided by the guides 45. At this time, while the tape 10 wound around the core 50 is being wound, the cells 101 are introduced into the tape 10 being wound around the core 60 inside the housing 40 via the window 44*a*.

Specifically, as shown in FIG. 14, the cell suspension injector 110 (or the housing 40) is moved such that the cell suspension injector 110 is arranged over the window 44*a*. Then, the cell suspension 101*a* is sprayed by the cell suspension injector 110 from the upper side (the Z1 direction side in FIG. 14) onto the tape 10 that moves under the window 44*a* while the inner circumferential surface 1*a* faces upward. Thus, the cells 101 are seeded in the wells 2 of the tape 10. In this step, the window 44*a* is opened in order to introduce the cell suspension 101*a* into the housing 40. In addition, in this step, the side surface 44 provided with the window 44*a* is directed upward.

In the third embodiment, in the step of introducing the cells 101, the cells 101 are introduced into the tape 10 being wound around the core 60 inside the housing 40 in a state in which the housing 40 is filled with a culture solution. That is, the cells 101 (cell suspension 101*a*) are seeded (introduced) in the wells 2 in a state in which at least the wells 2 of the tape 10 do not contain air bubbles (air). The culture solution is an example of a "solution" in the claims.

Then, as shown in FIG. 19, the tape 10 is wound around the core 60 after the cells 101 are seeded in the wells 2 in step S13. That is, the tape 10 into which the cells 101 have been introduced (seeded) is wound around the core 60 inside the housing 40. Specifically, as shown in FIG. 14, the tape 10 into which the cells 101 have been introduced (seeded) under (on the Z2 direction side in FIG. 14) the window 44*a* is wound around the core 60 while being guided by the guides 45, and finally substantially all the tape 10 is wound around the core 60.

Then, as shown in FIG. 19, the culture solution is introduced into the tape 10 so as to flow through each of the plurality of wells 2 in step S14. Specifically, as shown in FIG. 17, the culture solution is introduced into the tape 10 wound around the core 60 inside the housing 40 after the cells 101 are introduced (seeded) into the tape 10 such that the culture solution flows through each of the plurality of wells 2.

More specifically, as shown in FIG. 17, the culture solution is introduced into the conduit 60*d* (see FIG. 16) of the core 60 via the tube 70. In this case, the tube 70 and the first side portion 73*b* of the tube 73 are connected to each other, and the tube 71 and the second side portion 73*c* of the tube 73 are connected to each other.

Then, the culture solution introduced into the tape 10 via the conduit 60*d* (see FIG. 16) and flowing through each of the plurality of wells 2 is suctioned out through the conduit 60*e* (see FIG. 16) of the core 60 via the tube 71. The culture solution suctioned out through the conduit 60*e* of the core 60 is sent to the liquid storage 81 via the tube 71 and the second side portion 73*c* of the tube 73, and is stored in the liquid storage 81. Then, the culture solution stored in the liquid storage 81 is again delivered by the pump unit 80 to the conduit 60*d* of the core 60 via the first side portion 73*b* of the tube 73 and the tube 70. In this step, the culture solution is introduced in a state in which the protruding end 60*a* (side surface 41) of the core 60 faces upward (in a Z1 direction in FIG. 17). Furthermore, in this step, the window 44*a* is closed.

In the third embodiment, the step of flowing the culture solution through each of the plurality of wells 2 includes a step of flowing the culture solution through each of the plurality of wells 2 of the tape 10 wound around the core 60 inside the housing 40 in a state in which the culture solution has been discharged from the housing 40 after the cells 101 are introduced (seeded) into the tape 10. Specifically, the step of introducing the culture solution into each of the plurality of wells 2 (tape 10) is performed in a state in which the culture solution is discharged such that the housing 40 is filled with air. The culture solution in the housing 40 is discharged from the window 44*a* or a discharge port (not shown).

Then, as shown in FIG. 19, while the tape 10 wound around the core 60 is wound around the core 50 after the culture solution flows through the tape 10, the cells 101 are picked from the tape 10 being wound around the core 50 inside the housing 40 via the window 44*a* in step S15.

Specifically, as shown in FIG. 18, the cell suction nozzle 120 (or the housing 40) is moved such that the cell suction nozzle 120 is arranged over (on the Z1 direction side in FIG. 18) the window 44*a*. Then, the cells 101 seeded in the wells 2 of the tape 10 that moves under the window 44*a* while the inner circumferential surface 1*a* faces upward are suctioned by the cell suction nozzle 120 from above. Thus, the cells 101 in the wells 2 of the tape 10 are picked. In this step, the window 44*a* is opened to suction the cells 101. In addition, in this step, the side surface 44 provided with the window 44*a* is directed upward.

In the third embodiment, in the step of picking the cells 101, the cells 101 are picked from the tape 10 being wound around the core 50 inside the housing 40 in a state in which the housing 40 is filled with the culture solution after the culture solution flows through each of the plurality of wells 2. That is, the cells 101 are picked in a state in which at least the wells 2 of the tape 10 do not contain air bubbles (air). The culture solution is an example of a "solution" in the claims.

The remaining configurations of the third embodiment are similar to those of the first embodiment.

Advantages of Third Embodiment

According to the third embodiment, the following advantages are obtained.

According to the third embodiment, as described above, in the cell culture device 500, the housing 40 includes the window 44a adjusted for the cells 101 to be introduced into the tape 10 being wound around the core 60 from the core 50 inside the housing 40 and adjusted for the cells 101 to be picked from the tape 10 being wound around the core 50 from the core 60 inside the housing 40. Accordingly, the core 50 and the core 60 are used such that both the introduction of the cells 101 and the picking of the cells 101 can be performed. Consequently, the configuration of the cell culture device 500 can be simplified as compared with a case in which one of the introduction of the cells 101 and the picking of the cells 101 is performed using a member other than the core 50 and the core 60.

Furthermore, the introduction of the cells 101 and the picking of the cells 101 are performed via the window 44a of the housing 40 such that both the introduction of the cells 101 and the picking of the cells 101 can be performed while the tape 10 is placed inside the housing 40. Consequently, as compared with a case in which the tape 10 is moved to the outside of the housing 40 and one of the introduction of the cells 101 and the picking of the cells 101 is performed, a device space can be saved while the configuration of the cell culture device 500 can be further simplified.

According to the third embodiment, as described above, in the cell culture device 500, the housing 40 includes the guides 45 that guide the tape 10 being wound around the core 50 and the core 60 such that the tape 10 is exposed via the window 44a inside the housing 40. Accordingly, the tape 10 being wound around the core 50 and the core 60 is exposed via the window 44a by the guides 45, and thus the introduction of the cells 101 and the picking of the cells 101 performed on the tape 10 via the window 44a can be facilitated.

According to the third embodiment, as described above, the cell culture device 500 includes the cell suspension injector 110 configured to introduce the cells 101 via the window 44a into each of the plurality of wells 2 of the tape 10 being wound around the core 60 from the core 50 while being guided by the guides 45. The cell culture device 500 further includes the cell suction nozzle 120 configured to pick the cells 101 via the window 44a from the plurality of wells 2 of the tape 10 being wound around the core 50 from the core 60 while being guided by the guides 45. Accordingly, the cell suspension injector 110 is used such that the cells 101 can be easily introduced into the wells 2 of the tape 10 as compared with a case in which the cells 101 are introduced into the wells 2 by manually dropping the cell suspension 101a. Furthermore, the cell suction nozzle 120 is used such that the cells 101 can be easily picked from the wells 2 as compared with a case in which the cells 101 settle downward in the housing 40 due to their own weights and are collected from the housing 40.

According to the third embodiment, as described above, in the cell culture device 500, the window 44a is configured to be openable and closable. Accordingly, the housing 40 can be easily switched between a closed state and an open state.

According to the third embodiment, as described above, the cell culture method includes winding the tape around the core 50. Furthermore, seeding the cells 101 includes introducing the cells 101 into the tape 10 being wound around the core 60 inside the housing 40 via the window 44a provided on the housing 40 while the tape 10 wound around the core 50 is wound around the core 60. In addition, winding the tape 10 after seeding the cells 101 includes winding the tape 10 around the core 60 inside the housing 40 after introducing the cells 101 into the tape 10. Moreover, flowing the culture solution through each of the plurality of wells 2 includes flowing the culture solution through each of the plurality of wells 2 by introducing the culture solution into the tape 10 wound around the core 60 inside the housing 40 after introducing the cells 101 into the tape 10. Accordingly, each of introducing the cells 101 and flowing the culture solution can be performed while the tape 10 is placed inside the housing 40. Consequently, as compared with a case in which the tape 10 is moved to the outside of the housing 40 and one of introducing the cells 101 and flowing the culture solution is performed, the working time required to perform cell culture can be shortened by the time required to move the tape 10.

According to the third embodiment, as described above, the cell culture method includes picking the cells 101 via the window 44a from the tape 10 being wound around the core 50 inside the housing 40 while winding, around the core 50, the tape 10 wound around the core 60 after flowing the culture solution through the tape 10. Accordingly, the core 50 and the core 60 are used such that both the introduction of the cells 101 and the picking of the cells 101 can be performed. Consequently, it is possible to provide the cell culture method that enables simplification of the configuration of the cell culture device 500 as compared with a case in which one of the introduction of the cells 101 and the picking of the cells 101 is performed using a member other than the core 50 and the core 60.

According to the third embodiment, as described above, introducing the cells 101 includes introducing the cells 101 into the tape 10 being wound around the core 60 inside the housing 40 in a state in which the housing 40 is filled with the culture solution. Furthermore, flowing the culture solution through each of the plurality of wells 2 includes flowing the culture solution through each of the plurality of wells 2 of the tape 10 wound around the core 60 inside the housing 40 in a state in which the culture solution has been discharged from the housing 40 after introducing the cells 101 into the tape 10. In addition, picking the cells 101 includes picking the cells 101 from the tape 10 being wound around the core 50 inside the housing 40 in a state in which the housing 40 is filled with the culture solution after flowing the culture solution through each of the plurality of wells 2. Accordingly, the cells 101 are introduced into the tape 10 in a state in which the housing 40 is filled with the culture solution such that the cells 101 can be introduced (seeded) into the wells 2 while inclusion of air bubbles in the wells 2 of tape 10 is significantly reduced or prevented. Thus, seeding of the cells 101 in the wells 2 can be more reliably performed. Furthermore, the culture solution flows through the wells 2 in a state in which the culture solution inside the housing 40 has been discharged such that as compared with a case in which the housing 40 is filled with the culture solution such that the tape 10 is immersed in the culture solution, the culture solution in the wells 2 can be more efficiently circulated. In addition, the cells 101 are picked from the tape 10 in a state in which the housing 40 is filled with the culture solution such that the cells 101 can be picked from the housing 40 while exposure of the cultured cells 101 to the air is significantly reduced or prevented.

The remaining advantages of the third embodiment are similar to those of the first embodiment.

Modified Examples

The embodiments disclosed this time must be considered as illustrative in all points and not restrictive. The scope of the present invention is not shown by the above description of the embodiments but by the scope of claims for patent, and all modifications (modified examples) within the meaning and scope equivalent to the scope of claims for patent are further included. Furthermore, a new embodiment may be made by combining the arbitrary configuration of the first embodiment and the arbitrary configuration of the second embodiment.

For example, while the example in which the plurality of wells and the culture solution conduits are arranged on the inner circumferential side of the band-shaped member (tape 10) and are covered by the outer circumferential surface of the band-shaped member (tape 10) wound on the inner circumferential side of the plurality of wells and the culture solution conduits has been shown in each of the aforementioned first to third embodiments, the present invention is not limited to this. For example, the plurality of wells and the culture solution conduits may be arranged on the outer circumferential side of the band-shaped member (tape 10) and be covered by the inner circumferential surface of the band-shaped member (tape 10) wound on the outer circumferential side of the plurality of wells and the culture solution conduits. In this case, the plurality of wells and the culture solution conduits may not be provided on the circumferential surface of the band-shaped member (tape 10) wound on the outermost circumference.

While the example in which at the time of collecting the cells, the cells are suctioned by the cell suction unit (cell suction nozzle 9) to be collected has been shown in the aforementioned second embodiment, the present invention is not limited to this. For example, the cells may be directly collected (picked) using an instrument.

Figure 20:
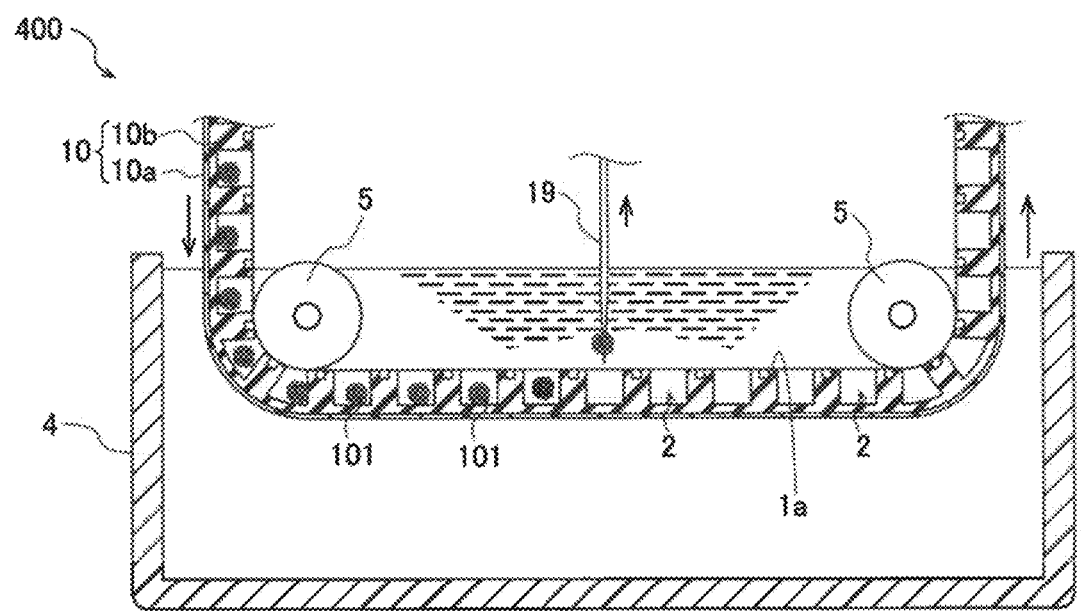
FIG. 20 is a diagram for illustrating a cell collection method in a cell culture device according to a modified example of the second embodiment.

Specifically, as shown in FIG. 20, a cell culture device 400 includes a cell picking needle 19 that picks cells 101 from a plurality of wells 2 of a tape 10 that passes through a culture solution in a collection container 4. More specifically, the cell picking needle 19 is configured to pick the cells 101 from the wells 2 of the tape 10 that passes through the culture solution in the collection container 4 under the cell picking needle 19.

That is, the cell picking needle 19 is configured to move downward and pierce the cells 101 when the cells 101 pass under the cell picking needle 19. Furthermore, the cell picking needle 19 is configured to pierce the cells 101 and then move upward to collect the cells 101. In the cell culture device 400, a plurality of cell picking needles 19 may be provided in the width direction (the upward-downward direction in FIG. 13) of the tape 10, or one cell picking needle 19 may be provided to be movable in the width direction of the tape 10. The cell picking needle 19 is an example of a "first cell picking unit" in the claims.

While the example in which the opening of the cell suction unit (cell suction nozzle 9) has a length corresponding to the length of the band-shaped member (tape 10) in the width direction has been shown in the aforementioned second embodiment, the present invention is not limited to this. For example, the cell suction unit (cell suction nozzle 9) may be configured to be movable in the width direction of the band-shaped member (tape 10), and may be configured to move above a well (cell) to be picked.

While the example in which the three connection conduit portions are connected to each of the plurality of wells has been shown in each of the aforementioned first to third embodiments, the present invention is not limited to this. For example, as shown in FIG. 21(a), only one connection conduit portion 132b may be connected to each of the plurality of wells 2. In this case, the culture solution flows into each of the plurality of wells 2 through a connection conduit portion 132a that surrounds each of the plurality of wells 2.

Alternatively, as shown in FIG. 21(b), only two connection conduit portions 232a may be connected to each of the plurality of wells 2. In this case, the culture solution flows into each of the plurality of wells 2 through a connection conduit portion 232b that surrounds each of the plurality of wells 2. The connection conduit portions 232a each have a trapezoidal shape that tapers toward the well 2 as viewed in a direction orthogonal to the inner circumferential surface 1a.

Alternatively, as shown in FIG. 21(c), only one connection conduit portion 332b may be connected to each of the plurality of wells 2. In this case, the culture solution flows into each of the plurality of wells 2 through a connection conduit portion 332a that surrounds each of the plurality of wells 2. The conduit width W2 of the connection conduit portion 332b is larger than the conduit width W3 of the connection conduit portion 332a.

While the example in which the culture solution is stored in the collection container (housing) has been shown in each of the aforementioned first to third embodiments, the present invention is not limited to this. For example, a buffer solution (a buffer solution in which a fluctuation in the hydrogen ion concentration is relatively small) may be stored in the collection container (housing).

While the example in which the opening 9a of the cell suction unit (cell suction nozzle 9) has a rectangular shape has been shown in the aforementioned second embodiment, the present invention is not limited to this. For example, the opening 9a may have a V-shape or a wavy shape so as to correspond to the plurality of wells arranged in a staggered manner, for example. The cell suction nozzle 120 according to the third embodiment may have the same configuration.

While the example in which the plurality of wells are provided in a staggered manner on the inner circumferential surface of the band-shaped member (tape 10) has been shown in each of the aforementioned first to third embodiments, the present invention is not limited to this. For example, the plurality of wells may be provided in a matrix on the inner circumferential surface of the band-shaped member (tape 10). Note that the matrix refers to an arrangement in which wells in adjacent rows are not misaligned in a predetermined direction when a plurality of rows of wells arranged along the predetermined direction are arranged side by side so as to be adjacent to each other along a direction orthogonal to the predetermined direction.

While the example in which the inner circumferential surface of the band-shaped member (tape 10) is non-adhesive to cells has been shown in each of the aforementioned first to third embodiments, the present invention is not limited to this. For example, the inner circumferential surface of the band-shaped member (tape 10) may be adhesive to cells.

While the example in which the plurality of wells and the culture solution conduits are not provided on the inner circumferential surface of the band-shaped member (tape 10) wound on the innermost circumference of the band-shaped member (tape 10) circumferentially wound has been shown in each of the aforementioned first to third embodiments, the present invention is not limited to this. For example, the plurality of wells and the culture solution conduits may be provided on the inner circumferential surface of the band-shaped member (tape 10) wound on the innermost circumference. In this case, the plurality of wells and the culture solution conduits provided on the inner circumferential surface of the band-shaped member (tape 10) wound on the innermost circumference are covered by the circumferential surface of the core. Thus, the core can significantly reduce or prevent leakage of the culture solution from the plurality of wells and the culture solution conduits provided on the inner circumferential surface of the band-shaped member wound on the innermost circumference.

Figure 22:
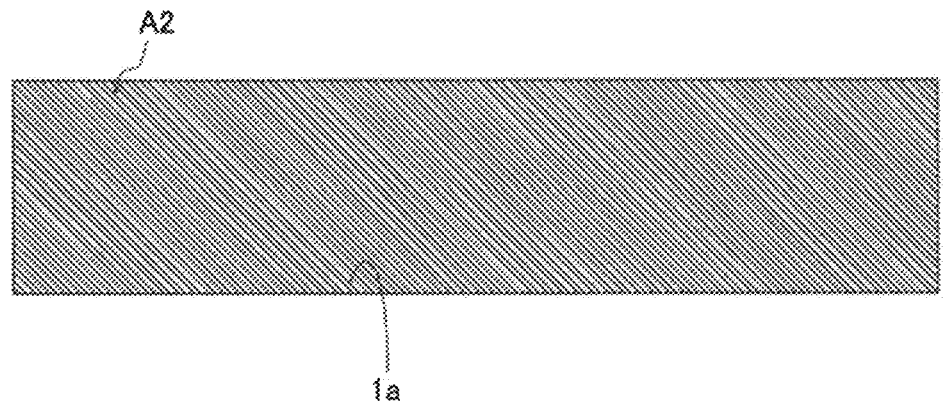
FIG. 22 is a diagram showing the arrangement of a well group on the inner circumferential surface of a tape in a cell culture device according to a modified example of the first to third embodiments.

While the example in which the plurality of well groups A1 are provided on the inner circumferential surface 1a of the band-shaped member (tape 10) has been shown in each of the aforementioned first to third embodiments, the present invention is not limited to this. For example, a single well group A2 (see a hatched portion in FIG. 22) in which all wells 2 are connected to each other by culture solution conduits 3 may be provided on the inner circumferential surface 1a.

While the example in which both ends of the core 50 (second core, first side core) protrude from the housing 40 has been shown in the aforementioned third embodiment, the present invention is not limited to this. For example, only one end of the core 50 (second core, first side core) may protrude from the housing 40, or both ends may not protrude from the housing 40. Similarly, only one end of the core 60 (third core, second side core) may protrude from the housing 40.

While the example in which the cell suspension 101a is introduced into the housing 40 in a state in which the housing 40 is filled with the culture solution has been shown in the aforementioned third embodiment, the present invention is not limited to this. For example, the cell suspension 101a may be introduced into the housing 40 in a state in which the housing 40 is not filled with the culture solution (in a state in which the housing 40 is filled with air).

While the example in which the two guides 45 are provided has been shown in the aforementioned third embodiment, the present invention is not limited to this. For example, one or three or more guides 45 may be provided.

While the example in which the cells 101 are seeded by spraying the cell suspension has been shown in each of the aforementioned first to third embodiments, the present invention is not limited to this. For example, the cells 101 may be seeded by dropping the cell suspension into the wells 2.

Figure 23:
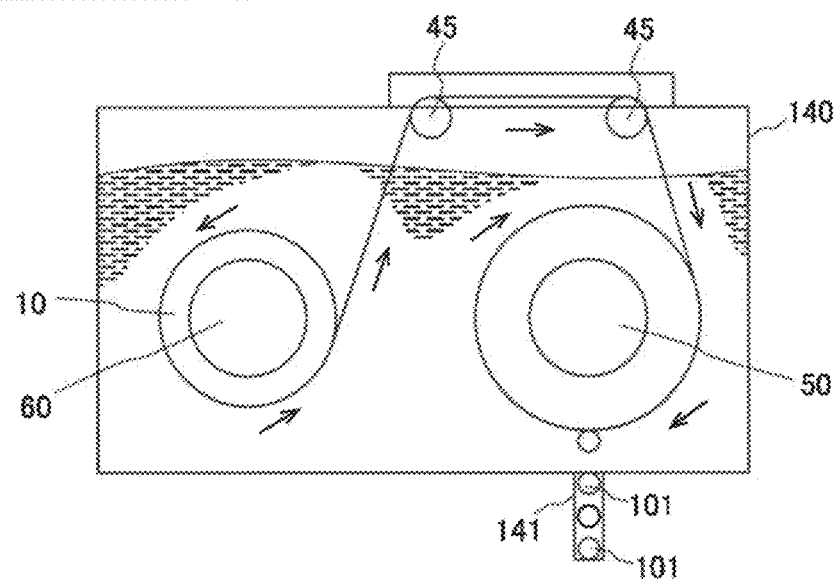
FIG. 23 is a front view showing a housing of a cell culture device according to a modified example of the third embodiment.

While the example in which the cells 101 are picked by the cell suction nozzle 120 (second cell picking unit) has been shown in the aforementioned third embodiment, the present invention is not limited to this. For example, as shown in FIG. 23, cells 101 may settle in a culture solution (solution) of a housing 140 due to their own weights from wells 2 of a tape 10 (band-shaped member) being wound around a core 50 (second core) (first side core) to be collected. In this case, the housing 140 may include a cell discharger 141 configured to discharge the cells 101 that settle in the culture solution (solution) of the housing 140 to the outside of the housing 140.

DESCRIPTION OF REFERENCE NUMERALS

1a: inner circumferential surface
1b: outer circumferential surface
2: well
2a: opening
3: culture solution conduit
4: collection container
9: cell suction nozzle (first cell picking unit) (cell suction unit)
10: tape (band-shaped member)
10c: end (upper end)
10d: end (lower end)
19: cell picking needle (first cell picking unit)
20: core (first core)
30: introduction conduit
31: discharge conduit
32: connection conduit
40, 140: housing
44a: window (opening)
45: guide
50: core (second core) (first side core)
60: core (third core) (second side core)
100, 300, 400, 500: cell culture device
101: cell
110: cell suspension injector (cell introduction unit)
120: cell suction nozzle (second cell picking unit)
Z: direction (vertical direction)
α, α1, α2: central axis

The invention claimed is:

1. A cell culture device comprising:
a band-shaped flexible member, the band-shaped member being configured to be circumferentially windable, wherein
in a state in which the band-shaped member is circumferentially wound, the band-shaped member has an inner circumferential surface and an outer circumferential surface, at least one of which is provided with a plurality of wells each having a concave shape, the plurality of wells adjusted for cells to be cultured therein,
at least some of the plurality of wells are connected to each other by a culture solution conduit adjusted for a culture solution to flow therethrough, and
the plurality of wells and the culture solution conduit are covered by directly contacting the outer circumferential surface of the band-shaped member wound on an inner circumferential side of the plurality of wells and the culture solution conduit, or by directly contacting the inner circumferential surface of the band-shaped member wound on an outer circumferential side of the plurality of wells and the culture solution conduit,
wherein the culture solution conduit includes a connection conduit that connect at least some of the plurality of wells,
wherein the connection conduit connects the lower wells from the upper portions of each of the plurality of wells and is inclined upward, and
wherein the plurality of wells are provided in a staggered manner on a circumferential surface of the band-shaped member.

2. The cell culture device according to claim 1, wherein
neither the plurality of wells nor the culture solution
conduit is provided on the inner circumferential surface
of the band-shaped member wound on an innermost
circumference of the band-shaped member circumferentially wound; and
the plurality of wells and the culture solution conduit are
provided on the inner circumferential surface of the
band-shaped member wound on an outer circumferential side of the band-shaped member wound on the
innermost circumference.

3. The cell culture device according to claim 1, further comprising:
a first core configured to extend along a central axis of a
winding of the band-shaped member; wherein
the plurality of wells and the culture solution conduit
provided on the inner circumferential surface of the
band-shaped member wound on an innermost circumference of the band-shaped member circumferentially
wound are covered by a circumferential surface of the
first core.

4. The cell culture device according to claim 1, wherein
in a state in which the band-shaped member circumferentially wound is arranged such that a central axis of a winding
is along a vertical direction, the culture solution conduit
includes an introduction conduit configured to connect the
plurality of wells arranged at an upper end of the band-shaped member and in a vicinity of the upper end, the
introduction conduit being adjusted for the culture solution
to be introduced thereinto, a discharge conduit configured to
connect the plurality of wells arranged at a lower end of the
band-shaped member and in a vicinity of the lower end, the
discharge conduit being adjusted for the culture solution to
be discharged therethrough.

5. The cell culture device according to claim 4, wherein
the connection conduit is configured to connect upper portions of the plurality of wells to each other in the state in
which the band-shaped member circumferentially wound is
arranged such that the central axis of the winding is along
the vertical direction.

6. The cell culture device according to claim 4, wherein
in the state in which the band-shaped member circumferentially wound is arranged such that the central axis of the
winding is along the vertical direction, the introduction
conduit is connected to an upper portion of each of the
plurality of wells arranged in the vicinity of the upper end,
and the discharge conduit is connected to an upper portion
of each of the plurality of wells arranged in the vicinity of
the lower end via the connection conduit.

7. The cell culture device according to claim 1, wherein
a circumferential surface of the band-shaped member provided with the plurality of wells is non-adhesive to the cells.

8. The cell culture device according to claim 1, further comprising:
a collection container configured to store a solution
through which the band-shaped member unwound from
a circumferentially wound state passes, the collection
container being configured to collect the cells contained
in the wells of the band-shaped member that passes
through the solution.

9. The cell culture device according to claim 8, wherein
the collection container is configured to collect, from the
plurality of wells of the band-shaped member that passes
through the solution while openings of the plurality of wells
face downward, the cells that settle in the solution due to
their own weights.

10. The cell culture device according to claim 8, further comprising:
a first cell picking unit configured to pick the cells from
the plurality of wells of the band-shaped member that
passes through the solution while openings of the
plurality of wells face upward.

11. The cell culture device according to claim 10, wherein
the first cell picking unit includes a cell suction unit configured to suction the cells from the plurality of wells of the
band-shaped member that passes through the solution.

12. The cell culture device according to claim 1, further comprising:
a second core configured to extend along a central axis of
a winding of the band-shaped member;
a third core provided separately from the second core, the
third core being configured to extend along the central
axis of the winding of the band-shaped member, the
third core being adjusted for the band-shaped member
unwound from the second core to be wound therearound; and
a housing configured to house the band-shaped member,
at least a portion of the second core, and at least a
portion of the third core; wherein
the second core is adjusted for the band-shaped member
unwound from the third core to be wound therearound;
and
the housing includes an opening adjusted for the cells to
be introduced into the band-shaped member being
wound around the third core from the second core
inside the housing, the opening being adjusted for the
cells to be picked from the band-shaped member being
wound around the second core from the third core
inside the housing.

13. The cell culture device according to claim 12, wherein
the housing includes a guide configured to guide the band-shaped member being wound around the second core and the
third core such that the band-shaped member is exposed via
the opening inside the housing.

14. The cell culture device according to claim 13, further comprising:
a cell introduction unit configured to introduce the cells
via the opening into each of the plurality of wells of the
band-shaped member being wound around the third
core from the second core while being guided by the
guide; and
a second cell picking unit configured to pick the cells via
the opening from the plurality of wells of the band-shaped member being wound around the second core
from the third core while being guided by the guide.

15. The cell culture device according to claim 12, wherein
the opening is configured to be openable and closable.

* * * * *